(12) United States Patent
Colman et al.

(10) Patent No.: US 10,898,432 B2
(45) Date of Patent: Jan. 26, 2021

(54) FORMULATIONS AND METHODS FOR CONTROLLING THE REPRODUCTIVE CYCLE AND OVULATION

(71) Applicant: Proinvet Innovations S.A., Ciudad Autónoma de Buenos Aires (AR)

(72) Inventors: Juan Andrés Colman, Buenos Aires (AR); Daniel Roberto Sammartino, Ciudad Autónoma de Buenos Aires (AR)

(73) Assignees: Proinvet Innovations S.A., Ciudad Autonoma de Buenos Aires (AR); Proinvet Innovations LLC, Dover, DE (US)

( * ) Notice: Subject to any disclaimer, the term of this patent is extended or adjusted under 35 U.S.C. 154(b) by 0 days.

(21) Appl. No.: 15/767,633

(22) PCT Filed: Dec. 16, 2016

(86) PCT No.: PCT/US2016/067132
§ 371 (c)(1),
(2) Date: Apr. 11, 2018

(87) PCT Pub. No.: WO2017/106618
PCT Pub. Date: Jun. 22, 2017

(65) Prior Publication Data
US 2018/0289614 A1  Oct. 11, 2018

(30) Foreign Application Priority Data
Dec. 18, 2015 (WO) ................ PCT/US2015/066863

(51) Int. Cl.
*A61K 9/00* (2006.01)
*A61K 31/57* (2006.01)
(Continued)

(52) U.S. Cl.
CPC .......... *A61K 9/0019* (2013.01); *A61K 9/0024* (2013.01); *A61K 9/06* (2013.01);
(Continued)

(58) Field of Classification Search
None
See application file for complete search history.

(56) References Cited

U.S. PATENT DOCUMENTS

| | | | |
|---|---|---|---|
| 4,599,227 A | 7/1986 | Dees et al. | |
| 6,287,588 B1 * | 9/2001 | Shih .................... | A61K 9/06 424/426 |

(Continued)

FOREIGN PATENT DOCUMENTS

| | | |
|---|---|---|
| CN | 101152186 A | 4/2008 |
| CN | 101856361 A | 10/2010 |

(Continued)

OTHER PUBLICATIONS

International Search Report and Written Opinion in corresponding International Patent Application No. PCT/US2015/0666863, dated May 6, 2016, in 10 pages.

(Continued)

*Primary Examiner* — Kyung S Chang
(74) *Attorney, Agent, or Firm* — Knobbe, Martens, Olson & Bear, LLP

(57) ABSTRACT

Hormone formulations, dosage units including the hormone formulations, and methods of use relate to a controlled release formulation, which includes hormones, e.g., progesterone. Formulations and methods are for controlling the reproductive cycle and/or ovulation of a female mammal, for example, to promote ovulation in a female mammal or synchronizing the ovulation or heat/estrus of a group of female mammals. In addition, formulations are for increasing the likelihood that a female mammal becomes pregnant, (Continued)

for example, after insemination or embryo transference. In addition, formulations are for reducing the anestrous period in a female mammal.

35 Claims, 3 Drawing Sheets

(51) Int. Cl.
  *A61K 9/16*  (2006.01)
  *A61K 9/06*  (2006.01)
  *A61K 31/565*  (2006.01)
  *A61K 31/568*  (2006.01)
  *A61P 15/08*  (2006.01)
  *A61K 38/09*  (2006.01)
  *A61K 31/557*  (2006.01)
  *A61K 9/10*  (2006.01)
  *A61K 9/107*  (2006.01)
  *A61K 9/51*  (2006.01)
  *A61K 9/08*  (2006.01)
  *A61K 47/10*  (2017.01)
  *A61K 47/12*  (2006.01)
  *A61K 47/14*  (2017.01)
  *A61K 47/34*  (2017.01)
  *A61K 47/38*  (2006.01)
  *A61K 47/44*  (2017.01)
  *A61M 5/178*  (2006.01)

(52) U.S. Cl.
  CPC ............... *A61K 9/08* (2013.01); *A61K 9/10* (2013.01); *A61K 9/107* (2013.01); *A61K 9/1617* (2013.01); *A61K 9/5123* (2013.01); *A61K 31/557* (2013.01); *A61K 31/565* (2013.01); *A61K 31/568* (2013.01); *A61K 31/57* (2013.01); *A61K 38/09* (2013.01); *A61K 47/10* (2013.01); *A61K 47/12* (2013.01); *A61K 47/14* (2013.01); *A61K 47/34* (2013.01); *A61K 47/38* (2013.01); *A61K 47/44* (2013.01); *A61M 5/178* (2013.01)

(56) References Cited

U.S. PATENT DOCUMENTS

| | | | |
|---|---|---|---|
| 6,589,549 | B2 | 7/2003 | Shih et al. |
| 7,157,102 | B1 | 1/2007 | Nuwayser |
| 2002/0013304 | A1 | 1/2002 | Wilson et al. |
| 2002/0131988 | A1 | 9/2002 | Foster et al. |
| 2003/0077297 | A1 | 4/2003 | Chen et al. |
| 2003/0137067 | A1 | 7/2003 | Cooper et al. |
| 2003/0180368 | A1 | 9/2003 | Dawson et al. |
| 2007/0104778 | A1 | 5/2007 | Zeng et al. |
| 2009/0220613 | A1 | 9/2009 | Odidi et al. |
| 2010/0255085 | A1 | 10/2010 | Liu et al. |
| 2013/0029947 | A1 | 1/2013 | Nachaegari et al. |
| 2013/0108737 | A1 | 5/2013 | Van Lengerich |
| 2014/0194677 | A1 | 7/2014 | Yoakum et al. |
| 2014/0271882 | A1 | 9/2014 | Giliyar et al. |
| 2015/0148323 | A1 | 5/2015 | Cacace et al. |
| 2015/0297733 | A1* | 10/2015 | Oberegger ........... A61K 31/568 604/310 |

FOREIGN PATENT DOCUMENTS

| | | |
|---|---|---|
| CN | 103284955 A | 9/2013 |
| CN | 103585103 A | 2/2014 |
| MX | PA06015172 | 4/2009 |
| WO | WO 91/19484 A1 | 12/1991 |
| WO | WO 97/040823 A1 | 11/1997 |
| WO | WO 1997/040823 A1 | 11/1997 |
| WO | WO 99/042110 A1 | 8/1999 |
| WO | WO 2001/070200 A1 | 9/2001 |
| WO | WO 2003/065924 A1 | 8/2003 |
| WO | WO 2005/048930 A1 | 6/2005 |
| WO | WO 2007/062483 A1 | 6/2007 |
| WO | WO 2010/085363 A1 | 7/2010 |
| WO | WO 2011/074931 A2 | 6/2011 |
| WO | WO 2012/156561 A1 | 11/2012 |
| WO | WO 2013/192250 A1 | 12/2013 |
| WO | WO 2017/105512 A1 | 6/2017 |
| WO | WO 2017/106618 A1 | 6/2017 |

OTHER PUBLICATIONS

International Search Report and Written Opinion in corresponding International Patent Application No. PCT/US2016/067132, dated Apr. 27, 2017, in 7 pages.

G.F. Duirs et al., "CIDR Systems in Suckling Beef Cows," Proceedings of the Australian society for reproductive biology, 19, 1987, p. 59.

Th Hornykiewytsch, "Intra-Vaginal Application System (INVAS) for Controlled Drug Release in Animals," Acta Pharmaceutica Technologica, vol. 34, No. 1, 1988, in 1 page.

K.L. MacMillan et al., "Onset of Oestrus and Fertility in Heifers Synchronized With Progesterone From a CIDR-Type B for Fifteen Days," Brief Communications, 11th International Congress on Animal Reproduction and Artificial Insemination, vol. 4, Jun. 26-30, 1988, in 5 pages.

K.L. MacMillan et al., "Plasma Progesterone Concentrations and Oestrus or Ovulation in Heifers Treated With a CIDR-Type B for at Least Seven Weeks," Proceedings of the Australian society for reproductive biology, 19, 1987, p. 61.

J.F. Roche et al., "The Use of Implants Containing Steroids for Growth Promotion and Control of Oestrus in Cattle," Animal Production, Journal of the British Society of Animal Production, vol. 13, 1971, p. 385.

J.F. Smith et al., "Synchronisation of Oestrus in Cattle," NZ Journal of Agriculture, Aug. 1974, pp. 26-31.

L.V. Swanson et al., "Effect of exogenous progesterone (P4) on follicular waves in dairy/beef heifers." Journal of Dairy Science, vol. 73, No. 12, Dec. 1990, p. 177.

S.P. Washburn et al., "Control of estrous cycles in mature dairy heifers with a progesterone-releasing device." American Dairy Science Association and American Society of Animal Science Combined Annual Meeting, Teaming Up for Animal Agriculture, Jul. 31-Aug. 4, 1989, in 3 pages.

R.A.S. Welch, "Mating Heifers With CIDR," Proceedings Ruakura Farmers' Conference, 37th Conference, 1985, pp. 105-107.

Nasim Ahmad et al., "Effect of Persistent Follicles on Early Embryonic Losses in Beef Cows," Biology of Reproduction, vol. 52, Issue 5, May 1, 1995, pp. 1129-1135.

Beck et al, "New long-acting injectable microcapsule contraceptive system," American Journal of Obstetrics and Gynecology, vol. 135, Issue 3, Oct. 1, 1979, pp. 419-426.

Burke et al., "Some effects of prematurely elevated concentrations of progesterone on luteal and follicular characteristics during the oestrous cycle in heifers," Animal Reproduction Science, vol. 35, Issues 1-2, Mar. 1994, pp. 27-39.

Burke et al., "Use of pregnant dairy cows in product development of the intravaginal progesterone releasing (CIDR) device," New Zealand Society of Animal Production online archive, Proceedings of the New Zealand Society of Animal Production, vol. 57, 1997, p. 242.

Carrick et al., "The Synchronization of Oestrus in Cattle with Progestagen-Impregnated Intravaginal Sponges," Reproduction, vol. 14, Issue 1, Aug. 1967, pp. 21-32.

S.E. Curl et al., "Synchronization of Estrus in Cattle with Subcutaneous Implants," Journal of Animal Science, vol. 27, No. 4, Jul. 1968, p. 1189.

Davis et al., "Induction of Lactation in Nonpregant Cows by Estradiol-17β and Progesterone from an Intravaginal Sponge," Journal of Dairy Science, vol. 66, Issue 3, Mar. 1983, pp. 450-457.

(56) References Cited

OTHER PUBLICATIONS

Marcia Espinosa, "Efecto de Diferentes Protocolos para IATF sobre las tasas de preñez aplicados en Ganado lechero," IRAC Cordoba, 2010, in 18 pages.

Hale et al., "Control of Sexual Activity in Ranch Cows by Intramuscular and Intravaginal Administration of Progestagens," Society for Reproduction and Fertility, vol. 18, Issue 2, Mar. 1969, pp. 193-199.

Heba F. Salem, "Sustained-release progesterone nanosuspension following intramuscular injection in ovariectomized rats," International Journal of Nanomedicine, vol. 5, published Nov. 10, 2010, pp. 943-954.

P.G. Hignett et al., "Synchronisation of Oestrus in Ayrshire Heifers by the use of Progestinated Intra-vaginal Pessaries," Veterinary Record, vol. 86, 1970, pp. 528-531.

Iwazumi et al., "Superovulation Using CIDR® in Holstein Cows," Journal of Reproduction and Development, vol. 40, No. 3, 1994, pp. 259-266.

D.R. Kerr et al., "Evaluation of three estrus synchronization regimens for use in extensively managed Bos indicus and Bos indicus/ taurus heifers in Northern Australia," Theriogenology, vol. 36, Issue 1, Jul. 1991, pp. 129-141.

MacMillan et al., "Combination treatments for synchronizing oestrus in dairy heifers," New Zealand Society of Animal Production online archive, Proceedings of the New Zealand Society of Animal Production, vol. 53, 1993, pp. 267-270.

MacMillan et al., "Detecting Estrus in Synchronized Heifers Using Tailpaint and an Aerosol Raddle," Theriogenology, vol. 30, Issue 6, Dec. 1988, pp. 1099-1114.

K.L. MacMillan et al., "Effects of varying the progesterone content of CIDR intravaginal devices and multiple CIDR treatments on plasma hormone concentrations and residual hormone content," Proceedings of the New Zealand Society of Animal Production, vol. 50, 1990, pp. 473-475.

K.L. MacMillan et al., "Some effects of using progesterone and oestradiol benzoate to stimulate oestrus and ovulation in dairy cows with anovulatory anoestrus," Proceedings of the New Zealand Society of Animal Production, vol. 55, 1995, pp. 239-241.

S. McDougall et al., "The effect of pretreatment with progesterone on the oestrous response to oestradiol-17β benzoate in the postpartum dairy cow," Proceedings of the New Zealand Society of Animal Production, vol. 52, 1992, pp. 157-160.

W.H. McMillan et al., "CIDR-B for managed reproduction in beef cows and heifers," Proceedings of the New Zealand Society of Animal Production, vol. 49, 1989, pp. 85-89.

S.R. McPhee et al., "Sychronisation of Oestrus in Dairy Cows Using Progesterone Administered by "Controlled Internal Drug Release" (CIDR) Devices," Proceedings of Australian Society of Animal Production, vol. 16, 1986, pp. 279-282.

Moore et al., "Effect of Progestagen intravaginal sponges and PMSG on synchronisation of oestrus in maiden heifers and on interval from calving on oestrus in beef cows," New Zealand Journal of Experimental Agriculture, vol. 8, Issues 3-4, 1980, pp. 199-203.

Rathbone et al., "Chapter 6—Design and development of controlled release intravaginal veterinary drug delivery systems," Controlled Release Veterinary Drug Delivery, Biological and Pharmaceutical Considerations, 2000, pp. 173-200.

Michael John Rathbone, "Delivering drugs to farmed animals using controlled release science and technology," International e-Journal of Science, Medicine and Education, 2012, pp. S118-S128.

Rathbone et al., Reengineering of a commercially available bovine intravaginal insert (CIDR insert) containing progesterone, Journal of Controlled Release, vol. 85, Issues 1-3, Dec. 13, 2002, pp. 105-115.

J.F. Roche, "Control of Time of Ovulation in Heifers Treated with Progesterone and Gonadotrophin-Releasing Hormone," Reproduction, vol. 43, Issue 3, Jun. 1975, pp. 471-477.

J.F. Roche, "Effect of Exogenous Progesterone on Time of Occurrence of the LH Surge in Heifers," Journal of Animal Science, vol. 52, Issue 3, Mar. 1981, pp. 580-586.

J.F. Roche, "Effect of Short-Term Progesterone Treatment on Oestrous Response and Fertility in Heifers," Reproduction, vol. 40, Issue 2, Oct. 1974, pp. 433-440.

J.F. Roche, "Fertility in cows after treatment with a prostaglandin analogue with or without progesterone," Reproduction, vol. 46, Issue 2, Mar. 1976, pp. 341-345.

J.F. Roche, "Retention rate in cows and heifers of intravaginal silastic coils impregnated with progesterone," Reproduction, vol. 46, Issue 1, Jan. 1976, pp. 253-255.

J.F. Roche, "Synchronization of Oestrus in Heifers with Implants of Progesterone," Reproduction, vol. 41, Issue 2, Dec. 1974, pp. 337-344.

Roche et al., "The long-term suppression of heat in cattle with implants of melengestrol acetate," Animal Science, vol. 16, Issue 3, Jun. 1973, pp. 245-250.

Savio et al., "Effects of induction of low plasma progesterone concentrations with a progesterone-releasing intravaginal device on follicular turnover and fertility in cattle," Reproduction, vol. 98, Issue 1, May 1993, pp. 77-84.

P.F. Burgess Scanlon, "Subcutaneous and oral applications of progestagens for control of estrus in heifers," Canadian Journal of Animal Science, vol. 51, Aug. 1971, pp. 540-541.

P.F. Scanlon et al., "Synchronization of Estrus in Cattle by Intravaginal Application of Progesterone With Estrogen Administration," Canadian Journal of Animal Science, vol. 51, Apr. 1971, pp. 250-251.

P.F. Scanlon et al., "Synchronization of Oestrus in Heifers by Intravaginal Application of Progesterone," The Veterinary Record, vol. 90, Issue 16, Apr. 15, 1972, pp. 440-441.

Shimizu et al., "Synchronization of Oestrus and Subsequent Fertility of Beef Cattle Following the Intravaginal Administration of Gestagen," Reproduction, vol. 13, Issue 3, Jun. 1967, pp. 555-558.

R.E. Short et al, "Induced or Sychronized Puberty in Heifers," Journal of Animal Science, vol. 43, Issue 6, Dec. 1976, pp. 1254-1258.

Sirois et al., "Lengthening the Bovine Estrous Cycle with Low Levels of Exogenous Progesterone: A Model for Studying Ovarian Follicular Dominance," Endocrinology, vol. 127, Issue 2, Aug. 1, 1990, pp. 916-925.

R.D. Smith et al., "Insemination of Holstein Heifers at a Preset Time after Estrous Cycle Synchronization Using Progesterone and Prostaglandin," Journal of Animal Science, vol. 58, Issue 4, Apr. 1984, pp. 792-800.

Smith et al., "Plasma levels of progesterone, Provera, oestradiol-17β, and 13,14-dihydro-15-keto-prostaglandin F in cows treated with Provera-impregnated intravaginal sponges," Reproduction, vol. 55, Issue 2, Mar. 1979, pp. 359-364.

J. Sreenan et al., "Retention of intravaginal sponge pessaries by cattle," The Veterinary Record, vol. 94, Jan. 12, 1974, pp. 45-47.

Valderrama et al., "Using nogestomet ear devices fixed-time insemination artificial in cattle double purpose, permanent nursing calf," CES Medicina Veterinaria y Zootecnia, vol. 7, No. 1, Jan./Jun. 2012, pp. 63-72.

Van Cleef et al., "Effects of Administering Progesterone at Selected Intervals After Insemination of Synchronized Heifers on Pregnancy Rates and Resynchronization of Returns to Service," Theriogenology, vol. 46, Issue 7, Nov. 1, 1996, pp. 1117-1130.

Van Cleef et al., "Effects of Postinsemination Progesterone Supplementation on Fertility and Subsequent Estrous Responses of Dairy Heifers," Theriogenology, vol. 36, Issue 5, Nov. 1991, pp. 795-807.

Van Cleef et al., "Plasma and milk progesterone and plasma LH in ovariectomized lactating cows treated with new or used controlled internal drug release devices," Animal Reproduction Science, vol. 27, Issues 2-3, Apr. 1992, pp. 91-106.

J.F. Roche et al., "The Use of Implants Containing Steroids for Growth Promotion and Control of Oestrus in Cattle," Animal Production, Journal of the British Society of Animal Production, vol. 13, 1971, pp. 385-387.

J.N. Wiltbank et al., "Control of Estrus and Ovulation using Subcutaneous Implants and Estrogens in Beef Cattle," Journal of Animal Science, vol. 33, Issue 3, Sep. 1971, pp. 600-606.

(56) References Cited

OTHER PUBLICATIONS

Winkler et al., "In Vitro and In Vivo Considerations of a Novel Matrix-Controlled Bovine Progesterone-Releasing Intravaginal Device," Journal of Pharmaceutical Sciences, vol. 66, No. 6, Jun. 1977, pp. 816-818.
Wishart et al., "Synchronization of Oestrus in Heifers Using Intra-Vaginal Pessaries Impregnated with SC-9880 and PMSG," Reproduction, vol. 17, Issue 2, pp. 285-289.
C.O. Woody et al., "Influence of Day of Estrous Cycle at Treatment on Response to Estrous Cycle Regulation by Norethandrolone Implants and Estradiol Valerate Injections," Journal of Animal Science, vol. 39, Issue 5, Nov. 1974, pp. 903-906.
Z.Z. Xu et al., "Reproductive performance of synchronized lactating dairy cows," New Zealand Society of Animal Production online archive, Proceedings of the New Zealand Society of Animal Production, vol. 55, 1995, p. 242-244.

\* cited by examiner

FORMULATIONS AND METHODS FOR CONTROLLING THE REPRODUCTIVE CYCLE AND OVULATION

FIELD

In the field of animal production, particularly in the meat and dairy industry, livestock reproductive management and control are essential. Reproductive management and control may be achieved through various hormonal intervention treatments applied to females.

Embodiments of this disclosure relate to hormone formulations, dosage forms comprising them, and the uses thereof. In particular, these embodiments relate to injectable controlled release formulation of hormones, e.g., progesterone. Other embodiments relate to formulations and methods for controlling the reproductive cycle and/or ovulation of a female mammal, for example, to reduce the anestrous period, promote ovulation in a female mammal or synchronizing the ovulation of a group of female mammals. In addition, still other embodiments relate to increasing the likelihood that a female mammal gets pregnant, for example, after insemination or embryo transference.

BACKGROUND

The reproductive cycle or estrous cycle may be defined as a series of physiological events that occur throughout an ovarian cycle of a female mammal. The estrous cycle represents a cyclical pattern of ovarian activity allowing females to move from a reproductive period of non-receptivity to receptivity period, thus allowing for pairing and subsequent establishment of gestation.

The changes that occur during the estrous cycle are regulated by a delicate interaction between hormones synthesized and secreted in the hypothalamus (gonadotropin-releasing hormone (GnRH)), the pituitary gland (follicle-stimulating hormone (FSH) and luteinizing hormone (LH)), the ovaries (progesterone (P4), estradiol (E2) and inhibin) and the uterus (prostaglandin F2 (PGF)), forming what is commonly known as hypothalamic-pituitary-gonadal-uterine axis. Control is exercised through a regulating system by which a hormone or secretor product may inhibit the release of another hormone (negative feedback) or, conversely, stimulate the synthesis and release of a larger amount of hormones (positive feedback).

Day 0 of the estrous cycle is the first day that heat is observed. However, from a physiological point of view, the estrous cycle begins after the destruction of the corpus luteum and ends with the destruction of the corpus luteum of the next cycle.

The estrous cycle may be divided into three phases:

1) Follicular or Luteal Regression Phase (Proestrus): This period begins with the regression of the corpus luteum of the previous corpus and ends with the manifestation of the estrous.

2) Pre-ovulatory Phase (Estrous and Metaestrous): This phase begins with receptivity to males and involves all changes allowing for ovulation and the beginning of the corpus luteum formation. In the formation of the corpus luteum (latinization) there are a series of morphological and biochemical changes allowing follicle cells to become luteal cells, changes that end with a functional corpus luteum.

3) Luteal Phase (Diestrum): This phase is characterized by the predominance of the corpus luteum. The maintenance of the corpus luteum, as well as the progesterone synthesis, is related to the LH hormone that is progesterotrophic and luteotrophic.

Other hormones that are attributed a role in progesterone synthesis are FSH and prostacyclin (PG12). The FSH hormone would bind to receptors located in the corpus luteus and would cause an increase in progesterone secretion. As regards PG12, in addition to stimulating luteal cells to produce progesterone, it would increase blood flow at the ovarian level, having a positive effect on the synthesis and secretion of progesterone.

It is well known in the art that control and synchronization of reproductive cycles and ovulation may provide great financial benefits in animal production. In order to control and synchronize reproductive cycles and ovulation, and to attempt increasing female fertility and the likelihood of pregnancy after insemination, several technologies have been developed allowing for control and manipulation of female hormonal levels by hormonal intervention programs, which are well known to a person skilled in the art.

For the sustained administration of hormones there are release matrices, usually made of polymeric materials, designed to continuously releasing medication over a sustained period of time. Polymeric matrices may take different forms and be located in various places of the animal to activate its function.

Currently, among the most used systems for synchronizing the reproductive cycle are controlled intravaginal hormone release devices. Intravaginal devices seek to achieve a sustained release of one or more hormones with the aim of encouraging the induction of the heat in animals. These devices need to be introduced into the animal's vagina to carry out its function. There is a great variety of intravaginal devices available in the market, among which may be mentioned, for example, intravaginal device PRID® (Progesterone Releasing Intravaginal Device), intravaginal device CIDR® (Controlled Internal Drug Release) or intravaginal device INVAS (Intravaginal Application System).

On the other hand, there are numerous sponge-type intravaginal devices. However, very few have been mass produced and ended up as commercial products. These devices have a greater specific surface area which increases the probability of microbial proliferation inside them which may cause an infection. This is the reason why these devices are often impregnated with antibiotics in addition to hormones.

There are several issues associated with the use of intravaginal devices, among which the most important are their low effectiveness and high infection and vaginitis rates, as well as the stress and discomfort they cause to the animal.

In addition, the use of these intravaginal devices involve a complex series of particular actions such as, for example, a) immobilizing the animal to have access to its back and clean the vaginal area of the animal to minimize infection risks; b) operators involved in this task must comply with safety standards required to avoid contact with the hormone of the device and prevent the spread of infections among the animals; c) the device must be inserted accurately since otherwise, the device may fall out of the vagina; and finally d) after the expiry of a period from about 7 to 15 days, the device must be removed with all the safety measures required and mentioned above, and then it must be discarded, for example, incinerated or buried, which implies an environmental impact. Consequently, the different steps that must be complied within the process imply on the one hand a repeated involvement of trained personnel, with its resulting costs, and on the other hand greater movement and intervention in animals, which causes more stress to the same.

Due to these downsides associated with the use of intravaginal devices, which could be considered disadvantageous in obtaining good results and for the health of animals, there have been attempts to develop other devices for the controlled-release of hormones, using, for example, subcutaneous implants.

The implantable delivery system consists of tubes, spheres, plates or discs of silicon, hydron or other non biodegradable biocompatible polymers, which have been filled with progesterone or another hormone. These devices are implanted under the skin of the animal through a minor surgery procedure in order to allow the release of hormone(s) directly into the body of the animal. Sometimes it is necessary to perform an additional surgery procedure to remove any exhausted systems.

There are some significant disadvantages associated with the use of these implantable systems. For example, the need to immobilize the animal to perform a surgery procedure, the requirement of aseptic conditions related to this type of procedures and the need to remove the exhausted implants.

Further, one of the main disadvantages of some existing products to control the reproductive cycle currently on the market is the low percentage of pregnancies obtained. This is because, among other factors, parameters and ovulation times differ greatly from one animal to another and, therefore, not all treated females have a mature ovum at the time insemination is carried out.

Injectable systems are an alternative to solve the difficulties and disadvantages associated with the use of intravaginal or implantable devices. The advantages of these systems would be, for example, that its application is very simple and do not require a rigorous aseptic conditioning of the injection area. In addition, the application of an injectable system enables dosing of each individual animal in particular by controlling the injected volume. Injectable systems also allow avoiding the step consisting of the removal of the delivery system once it is exhausted.

There are different injectable mechanisms and systems known for controlled delivery of hormones, such as progesterone. However, injectable hormone controlled release systems have not reached the goals needed to successfully replace intravaginal and implantable systems, which remain the most widely used devices.

The injectable systems known in the art have several drawbacks to be successfully applied in the control of the reproductive cycle of livestock.

Firstly, some known injectable systems produce a sustained hormone release which lasts for a very brief time (less than 48 h after administration). This is insufficient as it is well known in the art that a supply of progesterone to maintain plasma levels for periods from about 5 to 7 days is required to favor an appropriate follicular development and growth.

Secondly, some injectable systems for the controlled release of progesterone produce a sustained release over time that may last more than 30 days, without the possibility of interrupting such release. This is also inappropriate since it is required that progesterone levels decrease within a shorter time, to allow the ovulation of a dominant follicle developed.

On the other hand, some other known injectable systems, mainly those that were developed for use in human health use expensive components that significantly reduce its commercial application in animal production.

It is for all the above reasons that, even taking into account the great advantages offered by injectable systems, the same have failed so far to reach the effectiveness levels needed to get a place in the market. In fact, as mentioned above, intravaginal or implantable devices are most commonly used, since they meet the aim of generating a sustained release of hormone during a sufficiently long time, which may be finished voluntarily at the desired time by removing the device from the body of the animal.

In conclusion, it would be a significant improvement in the field of animal reproduction, to obtain an injectable system for the controlled release of hormones, particularly progesterone, that produces a sustained release of the hormone that is sufficiently extended in time to allow the appropriate follicular development differentiating a follicle over the rest, but at the same time not too prolonged, so as to allow a decrease of hormone levels in blood so that the dominant follicle matures (releasing LH) and ovulation occurs.

Accordingly there is a need in the market for systems to control the reproductive cycle and/or ovulation that are easily administered, for example, injectable systems, and at the same time achieve a comparable or better effectiveness than currently used intravaginal and implantable devices, providing better percentages of ovulation, better synchronization of ovulation times and higher pregnancy rates.

DETAILED DESCRIPTION OF EMBODIMENTS OF THE DISCLOSURE

Figure 1:
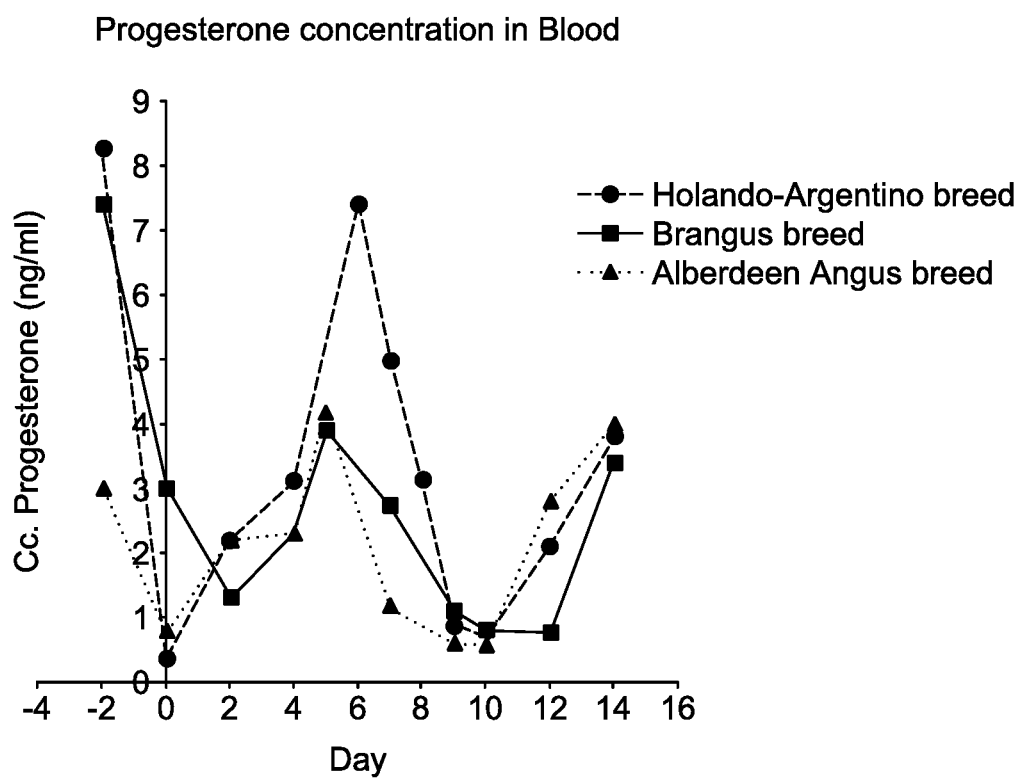
FIG. 1 is a graphic showing blood progesterone levels (ng/mL) in cows during the treatment. The dashed line with circular markers represent the average data obtained after treating a group of cows of the Holando-Argentino breed. The solid line with square markers represents the average data obtained following treatment of a group of cows of the Brangus breed. The dashed line with triangular markers represent the average data obtained after treating a group of cows of the Aberdeen Angus breed.

Progestagens are hormones that have progestational activity. In the present application, the term "progestagen" includes progesterones and all natural or synthetic analogs (sometimes referred to as progestins), medroxyprogesterone acetate (medrysone), norethindrone, norethindrone acetate, megestrol acetate, 17-α-hydroxyprogesterone caproate, norgestrel, and derivatives thereof.

The term "pharmaceutically acceptable" as used in the present application, means that the component is useful to prepare a pharmaceutical composition that generally is non-toxic and does not have undesirable biological effects and includes those accepted for veterinary use and/or pharmaceutical use in humans.

The term "surfactant" as used in the present application refers to a compound that reduces the surface tension of the medium in which it is located.

The term "carrier" as used in the present application means an inert medium in which there is an active agent, which facilitates its administration.

The term "pharmaceutically acceptable oily carrier" as used in the present application means any conventional vegetal or synthetic oil or a mixture thereof, which are acceptable for veterinary use or for pharmaceutical use in humans.

Prostaglandins are a group of substances of lipidic nature derived from 20-carbon fatty acids containing a cyclopentane ring and constitute a family of cellular mediators with diverse effects. In the present application, the term "prostaglandin" may refer to any existing natural or synthetic prostaglandin or any functional prostaglandin analogue, such as prostaglandin F2α or prostaglandin derivatives such as cloprostenol or a salt thereof The term "dosage unit" as used in the present application refers to any discrete physical unit suitable as unitary dosage for subjects to be treated; each of said units comprising a predetermined amount of active compound calculated to produce the desired therapeutic effect associated with the associated excipient or carrier.

The term "set of elements" or "kit" as used in the present application defines a package, assembly or container including one or more components of an embodiment the present disclosure and/or any other component related to an embodiment of the disclosure. It may also include instructions for use of such components.

The term "structure forming agent" as used in the present application refers to any excipient maintaining the physical stability of a formulation preventing the separation of its phases. Examples of structure forming agents of some embodiments of the present disclosure are, without limitation, cellulose, a cellulose derivative, microcrystalline cellulose, ethylcellulose, hydroxyethylcellulose, hydroxyethylmethylcellulose, hydroxyethylpropylcellulose, carboxymethylcellulose, guar gum, gum arabic, xanthan gum, chitosan, alginate, gelatin, carbopol, Carbopol 71G NF, Carbopol 971P NF, Carbopol 974P NF, Carbopol ETD 2020 NF, Carbopol 5984 ETD, Carbopol Ultrez 10, sodium starch glycolate, sodium corscarmelosa, alginic acid, pectin and combinations thereof.

The term "microparticle" as used in the present application refers to particles having a size of about 1 μm to 1000 μm. Said particles can include microcapsules (reservoir system) and microcrystals. In the case of microcapsules, the active substance is enclosed by a polymer or coating, whereas in the case of microcrystals the active component may be in a defined form or in an amorphous form in a non-compatible solvent.

The term "microcapsule" as used in the present application refers to a thin layer or coating of an amphipathic agent (comprising a hydrophobic portion and a hydrophilic portion, for example, a fatty acid), which may enclose an active substance both as a solid or dissolved in a solvent. Its size may vary between 1 and 500 microns and its aim may be, for example, to release the active ingredient into the surrounding environment in a slow or sustained manner over time.

The term "insemination" as used in the present application refers to the introduction of sperm into a female reproductive system.

The term "artificial insemination" as used in the present application refers to any reproductive technique consisting of depositing the sperm of a male inside the female reproductive system in order to fertilize it.

The term "fixed-time artificial insemination" as used in the present application refers to the artificial insemination of one or more animals at the same fixed-time without needing to detect the heat of said animal.

The term "artificial insemination at detected heat detection" as used in the present application refers to the artificial insemination of one or more animals where first the heat manifested by the animal is detected and then the animal is inseminated.

Gonadotropin releasing hormone (GnRH) is a hormone released by the hypothalamus whose center of action is the pituitary gland. It is a decapeptide that stimulates the release of gonadotrophin (luteinizing hormone, LH, and follicle stimulating hormone, FSH) from the anterior pituitary. In the present disclosure, when we refer to GnRH, we intend to include all existing natural or synthetic functional analogs and salts, for example, buserelin or buserelin acetate.

The term "livestock" as used in the present application refers to a group of animals that may be domesticated by humans for its exploitation and production.

The term "cattle" as used in the present application refers to a group of cows, bulls and bullocks that may be domesticated by humans for its exploitation and production.

The "reproductive cycle" of a female mammal is a number of physiological events occurring in the ovary at intervals of cyclic and regular time.

The terms "heat" and "estrous" as used in the present application refer to the sexual receptivity behavior of an animal.

The term "anestrous" as used in the present application refers to the state of sexual inactivity in female animals during which they exhibit no sexual receptivity behavior. Causes of anestrous include, for example, pregnancy, presence of offspring, season, stress, and pathologies, among others.

Equine Chorionic Gonadotropin hormone (eCG) is a glycoprotein produced by the endometrial cups of a pregnant mare with FSH (follicle stimulating hormone) function. In the present disclosure, with reference to an eCG, we intend to include all existing natural or synthetic functional analogs and salts.

The term "pharmaceutically acceptable gel forming agent" as used in the present application refers to any compound capable of gelling in a certain condition, which is acceptable for veterinary use or for pharmaceutical use in humans. Examples can include poloxamers, which are non-ionic tri-block copolymer compounds of a central hydrophobic chain of polyoxypropylene flanked by two hydrophilic polyoxyethylene chains. Some known trademarks of polymers are Synperonics, Pluronics, and Kolliphor. As the lengths of the polymer blocks may vary, there are many poloxamers with different properties. The term "poloxamer" followed by three digits gives information, where the first two digits multiplied by 100 are the approximate molecular mass of the polyoxypropylene core and the last digit multiplied by 10 is the percentage of polyoxyethylene. For example, Poloxamer P407, means Poloxamer with a polyoxypropylene molecular mass of 4000 g/mol and 70% of polyoxyethylene. Kolliphor P407, for example, is a commercial form of Poloxamer P407.

A first aspect of an embodiment of the present disclosure is to provide formulations for controlling the reproductive cycle and/or ovulation in a female mammal. For example, the formulations of the present disclosure can be used to reduce the anestrous period, promote ovulation in a female mammal and/or synchronizing the ovulation of a group of female mammals. In addition, they can be used to increase the likelihood that a female mammal gets pregnant, for example, after insemination or embryo transference. In an embodiment of this disclosure, the formulation comprises i) said one or more hormones; ii) said one or more pharmaceutically acceptable organic solvents; iii) optionally, said pharmaceutically acceptable oily carrier; iv) said one or more pharmaceutically acceptable fatty acids; v) optionally, said one or more pharmaceutically acceptable structure forming agents; vi) said one or more pharmaceutically acceptable surfactants; vii) said one or more pharmaceutically acceptable gel forming agents; and viii) water.

In an embodiment of the present disclosure, the formulations may comprise one or more natural or synthetic progestins, for example progesterone (P4), or an analogue or a salt or combinations of said hormone. In other embodiments of the present disclosure, the formulations may also comprise other hormones such as, for example, an estrogen, estradiol benzoate, estradiol cypionate, d-cloprostenol sodium, DL cloprostenol sodium, buserelin acetate. In another embodiment of the present disclosure, the formulation comprises progesterone or a salt or an analogue of said hormone. The progesterone or analogue or a salt thereof may comprise, for example, progesterone of natural or synthetic origin. Further, the progesterone may comprise BP grade (British Pharmacopoeia) or USP grade (US Pharmacopoeia) progesterone or any other commercial analogue.

In an embodiment of the present disclosure, said one or more pharmaceutically acceptable organic solvents may comprise, for example, ethanol, benzyl alcohol, benzyl benzoate, glycerol, glycerol formal, ethyl oleate, PEG400, propylene glycol, dimethylsulfoxide (DMSO), N-methylpyrrolidone, Miglyol, Miglyol 808, Miglyol 810, Miglyol 812, Miglyol 829, Miglyol 8108, Dynacetin 660, Softisan 649, Imwitor491, Imwitor 900 K, Imwitor 900 P, Imwitor 960 K, Imwitor 642, Imwitor 742, Imwitor 928, Imwitor 988, Imwitor 948, Softigen 701 or any other similar, or combinations thereof. In another embodiment of the present disclosure, the formulation comprises ethanol, benzyl alcohol, benzyl benzoate or a combination thereof, and even more preferably it comprises ethanol, benzyl alcohol and benzyl benzoate.

In an embodiment of the present disclosure, said optional pharmaceutically acceptable oily carrier may comprise, for example, flax oil, sesame oil, refined sesame oil, castor oil, palmitic acid, soybean oil, ethoxylated soybean oil, sunflower oil, corn oil, coconut oil, olive oil, almond oil, cotton oil, or combinations thereof. In another embodiment of the present disclosure, the formulation comprises sesame oil, preferably, refined sesame oil.

In an embodiment of the present disclosure, said one or more pharmaceutically acceptable fatty acids may comprise, for example, fatty acids of from 14 to 22 carbon atoms, and may be saturated or partially insaturated, but preferably saturated, fatty acids. In another embodiment, said one or more pharmaceutically acceptable fatty acids may comprise, for example, stearic acid, arachidonic acid, palmitic acid, miristic acid, oleic acid, linoleic acid, linolenic acid, arachidic acid, erucic acid or combinations thereof. In yet another embodiment, said one or more pharmaceutically acceptable fatty acids comprise stearic acid.

In an embodiment of the present disclosure, said optional one or more pharmaceutically acceptable structure forming agents may comprise, for example, cellulose or its derivatives, for example, microcrystalline cellulose, ethylcellulose, hydroxyethylcellulose, hydroxyethylmethylcellulose, hydroxyethylpropylcellulose, carboxymethylcellulose, guar gum, gum arabic, xanthan gum, chitosan, alginate, gelatin, Carbopol, Carbopol 71G NF, Carbopol 971P NF, Carbopol 974P NF, Carbopol ETD 2020 NF, Carbopol 5984 ETD, Carbopol Ultrez 10, sodium starch glycolate, sodium corscarmelosa, alginic acid, pectin or combinations thereof. In another embodiment of the present disclosure, the formulation comprises hydroxyethyl cellulose. In yet another embodiment of the present disclosure, the formulation comprises hydroxyethyl cellulose, gum arabic and xanthan gum.

In an embodiment of the present disclosure, said one or more pharmaceutically acceptable surfactants may comprise, for example, castor oil, for example, hydrogenated castor oil, ethoxylated castor oil, ethoxylated castor oil of from 15 to 60 moles of ethylene oxide, for example, ethoxylated castor oil at 40 moles of ethylene oxide, ethoxylated lauric alcohol of from 7 to 10 moles, Cremophor RH 40, Cremophor RH 60, Cremophor CO 455, Kolliphor EL, Lipocol oxo 650, Lipocol oxo 600, Solutol HS 15, Emulgin B1 PH, Lanette 20 PH, Lanette N PH, Polysorbate, Polysorbate 20 PH, Polysorbate 60 PH, Polysorbate 80 PH, ethoxylated fatty alcohols (of from 6 to 30 moles of ethylene oxide) derived from Capri alcohol, decyl alcohol, lauryl alcohol, isotridecyl alcohol, myristyl alcohol, ethyl alcohol, palmoleyl, stearyl, oleyl, elaidyl, petroselinyl, linolyl alcohol, linolenic, elaeostearyl alcohol, eicosyl, arachyl, gadoleyl, behenyl alcohol, erucyl alcohol, brassidyl or combinations thereof. In another embodiment, the formulation comprises castor oil, preferably, ethoxylated castor oil at 40 moles of ethylene oxide.

In an embodiment of the present disclosure, said one or more pharmaceutically acceptable gel forming agents may comprise, for example, sucrose acetate isobutyrate (SAIB), oxyethylenated and propoxyethylenated block copolymers, Pluronic F 127, Poloxamer, for example, Poloxamer P407, Kolliphor P188, Kolliphor P237, Kolliphor P338, Kolliphor P407, maleic acid or anhydride and methyl vinyl ether copolymer, modified acrilic polymers, PEG 3000, Macrogol 4000, Macrogol 6000, Poloxamine or combinations thereof. In another embodiment, the formulation comprises a thermo sensitive gel forming agent, preferably, Poloxamer P407 (for example, Kolliphor P407).

In another embodiment of the present disclosure, the formulation comprises: a) progesterone or an analogue or a salt thereof; b) benzyl alcohol; c) benzyl benzoate; d) ethanol; e) stearic acid; f) hydroxyethylcellulose; g) ethoxylated castor oil, at 40 moles of ethylene oxide; h) Poloxamer P407; i) refined sesame oil; and j) water.

In another embodiment of the present disclosure, the formulation comprises: a) progesterone or an analogue or a salt thereof; b) benzyl alcohol; c) benzyl benzoate; d) ethanol; e) stearic acid; f) hydroxyethylcellulose; g) ethoxylated castor oil, at 40 moles of ethylene oxide; h) Poloxamer P407; and i) water.

In another embodiment of the present disclosure, the formulation comprises: a) progesterone or an analogue or a salt thereof; b) benzyl alcohol; c) benzyl benzoate; d) ethanol; e) stearic acid; f) ethoxylated castor oil, at 40 moles of ethylene oxide; g) Poloxamer P407; h) refined sesame oil; and i) water.

In another embodiment of this disclosure, the formulations are controlled release formulations, wherein a portion of said one or more hormones is dissolved in a mixture comprising said one or more pharmaceutically acceptable organic solvents and, optionally, said pharmaceutically acceptable oily carrier to form a free portion; and a portion of said one or more hormones is enclosed by said one or more pharmaceutically acceptable fatty acids to form a enclosed portion. Said free and enclosed portions of said one or more hormones may be comprised in a matrix comprising: i) optionally, said one or more pharmaceutically acceptable structure forming agents, ii) said one or more pharmaceutically acceptable gel forming agents and iii) said one or more pharmaceutically acceptable surfactants.

In another embodiment of this disclosure, the controlled release formulation may comprise:

1) one or more natural or synthetic progestagens or salts thereof, preferably progesterone, dissolved in a mixture of i) said one or more pharmaceutically acceptable organic solvents, preferably ethanol, benzyl alcohol and benzyl benzoate, and ii) said pharmaceutically acceptable oily carrier, preferably refined sesame oil;

2) one or more natural or synthetic progestagens or salts thereof, preferably progesterone, forming microcapsules or microparticles enclosed by said one or more pharmaceutically acceptable fatty acid, preferably stearic acid; and 3) a matrix which includes said components 1) and 2), wherein said matrix comprises i) said one or more pharmaceutically acceptable structure forming agents, preferably hydroxyethylcellulose; ii) said one or more pharmaceutically acceptable gel forming agents, preferably Poloxamer P407; and iii) said one or more pharmaceutically acceptable surfactants, preferably ethoxylated castor oil, at 40 moles of ethylene oxide.

The controlled release formulation of an embodiment of this disclosure allows a controlled release of one or more hormones, for example, progesterone, into the bloodstream of a female mammal after its administration. First, there is a sustained blood concentration of said one or more hormones followed by a decrease in hormone concentration. For example, the decrease in blood concentration of the hormone may take place from about 5 to about 10 days after administration, and preferably from about 6 to 8 days after administration of the formulation Hormone concentrations in the blood and release times after administration of the formulation of an embodiment of this disclosure may vary depending on the characteristics of the animal to which the formulation is administered, the route by which the formulation is applied, or various other factors.

The formulations of an embodiment of this disclosure may optionally comprise a protective agent, for example, a pharmaceutically acceptable antioxidant agent. Said pharmaceutically acceptable antioxidant may comprise, for example, Vitamin E, Vitamin E TGPS (d-α-tocopherol propylene glycol 1000 succinate), Kolliphor TGPS, Butylated hydroxytoluene (BHT), butylated hydroxyanisole (BHA), sodium bisulphite, ascorbic acid, ascorbyl palmitate, Vitamin A, propyl gallate, monothioglycerol, sodium sulfoxilatoformal, or combinations thereof.

The water in the formulations of an embodiment of this disclosure may be replaced by any other liquid or aqueous solution, for example, a saline solution. The water in the formulations of an embodiment of this disclosure may be, for example, water or any acceptable solution or aqueous liquid for injections.

The formulations of an embodiment of this disclosure described above may comprise progesterone or an analogue or a salt thereof, at a concentration of from about 1 mg/mL to about 250 mg/mL, preferably from about 10 mg/mL to about 200 mg/mL, preferably from about 20 mg/mL to about 100 mg/mL, preferably from about 30 mg/mL to about 70 mg/mL, preferably from about 40 mg/mL to about 60 mg/mL, and more preferably about 50 mg/mL.

The formulations of an embodiment of this disclosure may also comprise benzyl alcohol at a concentration of up to about 1000 mg/mL, or from about 5 mg/mL to about 500 mg/mL, or from about 10 mg/mL to about 250 mg/mL, or from about 20 mg/mL to about 150 mg/mL, or from about 30 mg/mL to about 100 mg/mL, or from about 40 mg/mL to about 60 mg/mL, and preferably about 40 mg/mL.

The formulations of an embodiment of this disclosure may also comprise benzyl benzoate at a concentration of up to about 60 mg/mL, or from about 1 mg/mL to about 40 mg/mL, or from about 10 mg/mL to about 30 mg/mL, and preferably about 20 mg/mL.

The formulations of an embodiment of this disclosure may also comprise ethanol at a concentration of up to about 300 mg/mL, or from about 10 mg/mL to about 250 mg/mL, or from about 50 mg/mL to about 200 mg/mL, or from about 100 mg/mL and about 150 mg/mL preferably about 120 mg/mL.

The formulations of an embodiment of this disclosure may also comprise stearic acid at a concentration of up to about 60 mg/mL, or from about 1 mg/mL to about 40 mg/mL, or from about 10 mg/mL to about 30 mg/mL, preferably about 20 mg/mL.

The formulations of an embodiment of this disclosure may also comprise, optionally, hydroxyethylcellulose at a concentration of up to about 50 mg/mL, or up to about 40 mg/mL or up to about 30 mg/mL, or up to about 20 mg/mL or up to about 10 mg/mL, or from about 2 mg/mL to about 8 mg/mL, preferably about 4 mg/mL.

The formulations of an embodiment of this disclosure may also comprise ethoxylated castor oil, at 40 moles of ethylene oxide at a concentration of up to about 120 mg/mL, or from about 10 mg/mL to about 120 mg/mL, or from about 20 mg/mL to about 80 mg/mL, or from about 40 mg/mL to about 70 mg/mL, preferably about 100 mg/mL.

The formulations of an embodiment of this disclosure may also comprise Poloxamer P407 (for example, Kolliphor P407) at a concentration of up to about 120 mg/mL, or from about 10 mg/mL to about 100 mg/mL, or from about 50 mg/mL to about 90 mg/mL, or preferably or from about 50 mg/mL to about 90 mg/mL, preferably about 70 mg/mL.

The formulations of an embodiment of this disclosure may also comprise, optionally, refined sesame oil at a concentration of up to about 100 mg/mL, or from about 5 mg/mL to about 70 mg/mL, or from about 10 mg/mL to about 30 mg/mL, preferably about 20 mg/mL.

The formulations of an embodiment of this disclosure may also comprise water in the formulation in an amount of up to about 1000 mg/mL, or from about 100 mg/mL to about 900 mg/mL, or from about 200 mg/mL to about 800 mg/mL, preferably from about 500 mg/mL to about 600 mg/mL.

The formulations of an embodiment of this disclosure may comprise from about 1 mg/mL to about 250 mg/mL progesterone or an analogue or a salt thereof, up to about 1000 mg/mL benzyl alcohol, up to about 60 mg/mL benzyl benzoate, up to about 300 mg/mL ethanol, up to about 60 mg/mL stearic acid, up to about 50 mg/mL hydroxyethyl cellulose, up to about 120 mg/mL ethoxylated castor oil at 40 moles of ethylene oxide, up to about 120 mg/mL Poloxamer P407, up to about 100 mg/mL refined sesame oil, and up to about 1000 mg/mL water.

The formulations of an embodiment of this disclosure may comprise from about 1 mg/mL to about 250 mg/mL progesterone or an analogue or a salt thereof, up to about 1000 mg/mL benzyl alcohol, up to about 60 mg/mL benzyl benzoate, up to about 300 mg/mL ethanol, up to about 60 mg/mL stearic acid, up to about 50 mg/mL hydroxyethyl cellulose, up to about 120 mg/mL ethoxylated castor oil at 40 moles of ethylene oxide, up to about 120 mg/mL Poloxamer P407, and up to about 1000 mg/mL water.

The formulations of an embodiment of this disclosure may comprise from about 1 mg/mL to about 250 mg/mL progesterone or an analogue or a salt thereof, up to about 1000 mg/mL benzyl alcohol, up to about 60 mg/mL benzyl benzoate, up to about 300 mg/mL ethanol, up to about 60 mg/mL stearic acid, up to about 120 mg/mL ethoxylated castor oil at 40 moles of ethylene oxide, up to about 120 mg/mL Poloxamer P407, up to about 100 mg/mL refined sesame oil, and up to about 1000 mg/mL water.

The formulation of an embodiment of this disclosure may also further comprise, optionally, a pH adjusting agent. In any case, the pH of the final formulation may be adjusted to a value from about 4.0 to about 8.0, or from about 4.5 to about 7.5, preferably from about 5.0 to about 7.0. The preferred final pH of the formulation may be, for example, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0.

The formulation of an embodiment of this disclosure may be in the form of a solution, for example, a liquid solution, micellar solution, suspension, a two or more phase system, emulsion, for example, a microemulsion, miniemulsion, small particle emulsion or combinations thereof.

The formulation of an embodiment of this disclosure may be a sterile formulation. The formulation or the separate components thereof of an embodiment of this disclosure may be sterilized using different methods. Sterilization methods are well known in the art and may comprise, as appropriate, heat sterilization, sterilization by filtration, sterilization by UV radiation, gamma radiation sterilization, among others.

The formulations of an embodiment of this disclosure may be suitable for use as injectable formulations, but it should be understood that the formulations may be adapted for administration via different alternative routes. In the case of injectable formulations, these may be administered through the most appropriate route according to the characteristics of the animal, for example, parenteral, subcutaneous, intravenous, intradermal or intramuscular. One embodiment of this disclosure is an injectable formulation suitable for intramuscular administration.

The formulations of an embodiment of this disclosure may be useful for controlling the reproductive cycle and/or ovulation in a female mammal. The formulations of an embodiment of this disclosure may also be used to promote ovulation. Another use of the formulations of an embodiment of this disclosure may be to synchronize the ovulation or the heat of a group of female mammals. In addition, the formulations of an embodiment of this disclosure may be used to reduce the anestrous period. In addition, the formulations of an embodiment of this disclosure may be used to increase the likelihood that a female mammal gets pregnant. For example, the formulations of an embodiment of this disclosure may be used to increase the likelihood that a female mammal gets pregnant after insemination, which may be artificial or natural insemination. For example, the formulations of an embodiment of this disclosure may be used together with a fixed-time artificial insemination (FTAI) protocol or a heat detection insemination protocol. The formulations of an embodiment of this disclosure may be used also in ovarian superstimulation protocols to super-ovulate, they also may be used in ovarian puncture protocols for subsequent in vitro fertilization or to increase the likelihood of success of embryo transfer process.

Said female mammal may be, for example, a domestic or farm animal. For example, the female mammal may be a ruminant, such as cattle, pigs, goats, sheep, horses, camels, among others. For example, the female mammal may be a reproductively mature female bovine animal.

The formulations of an embodiment of this disclosure may be used in coordination with other treatments, such as other hormone treatments to achieve the desired objectives.

A second aspect of an embodiment of this disclosure provides a dosage unit comprising a formulation as described in the first aspect of an embodiment of the disclosure.

In one embodiment, the dosage unit may have a volume from about 1 mL to about 20 mL, or from about 2 mL to about 10 mL or from about 4 mL to about 5 mL.

The dosage unit in one embodiment may be housed in a container, for example, a bottle, vial, ampoule or syringe, among others. Therefore, an embodiment of the disclosure also provides a container prefilled with the required amount of the formulation described in the first aspect of an embodiment of the disclosure, for example, a syringe prefilled with the formulation.

Another aspect of an embodiment of this disclosure provides a set of elements (kit) comprising the formulation, dosage unit or prefilled container, for example, a prefilled syringe, as described above. The set of components (kit) of an embodiment of this disclosure may further comprise, for example, the instructions for using some or all the elements comprising it.

Still another aspect of an embodiment of this disclosure provides a process for preparing a formulation such as the one described in the first aspect of an embodiment of the disclosure. The process comprises combining each component of the formulation.

In one embodiment of this disclosure, the process for preparing the formulation comprises combining i) said one or more hormones; ii) said one or more pharmaceutically acceptable organic solvents; iii) optionally, said pharmaceutically acceptable oily carrier; iv) said one or more pharmaceutically acceptable fatty acids; v) optionally, said one or more pharmaceutically acceptable structure forming agents; vi) said one or more pharmaceutically acceptable surfactants; vii) said one or more pharmaceutically acceptable gel forming agents; and viii) water.

In another embodiment of this disclosure, the process for preparing the formulation comprises preparing mixtures comprising certain components separately which will be combined later. For example, the process for preparing the formulation of an embodiment of the present disclosure may comprise:

1) preparing a first solution (pre-product A) comprising said one or more pharmaceutically acceptable surfactants and water;

2) preparing a second solution comprising said one or more hormones, said one or more pharmaceutically acceptable fatty acids, said one or more pharmaceutically acceptable organic solvents, said one or more pharmaceutically acceptable gel forming agents and water, wherein said second solution is prepared by combination of mixture I (pre-product B) and mixture II (pre-product C), wherein a) mixture I (pre-product B) comprises said one or more hormones, said pharmaceutically acceptable fatty acids and said one or more pharmaceutically acceptable organic solvents; and b) mixture II (pre-product C) comprises said one or more pharmaceutically acceptable gel forming agents and water;

3) preparing a third solution (pre-product D) comprising said one or more hormones, said one or more pharmaceutically acceptable organic solvents and, optionally, said pharmaceutically acceptable oily carrier; and 4) optionally, preparing a fourth solution (pre-product E) comprising said one or more pharmaceutically acceptable structure forming agents and water;

5) combining said first solution with said second solution;

6) incorporating said third solution into the mixture obtained in step 5); and 7) optionally, adding said fourth solution to the mixture obtained in step 6).

In the processes of an embodiment of this disclosure, said first solution may comprise, for example, ethoxylated castor oil, at 40 moles of ethylene oxide and water; said mixture I may comprise, for example, progesterone or an analogue or a salt thereof, stearic acid and ethanol; said mixture II may comprise, for example, Poloxamer P407 (for example, Kolliphor P407) and water; said third solution may comprise, for example, progesterone or an analogue or a salt thereof, ethanol, benzyl alcohol, benzyl benzoate and, optionally, refined sesame oil; and said optional fourth solution may comprise, for example, hydroxyethylcellulose and water.

In the processes of an embodiment of this disclosure, optionally, a pharmaceutically acceptable antioxidant may be included in mixture I. The pharmaceutically acceptable antioxidant may be, for example, Vitamin E, Vitamin E TGPS (d-α-tocopherol propylene glycol 1000 succinate), Kolliphor TGPS, Butylated hydroxytoluene (BHT), Butylated hydroxyanisole (BHA), sodium bisulphite, ascorbic acid, ascorbyl palmitate, Vitamin A, propyl gallate, monothioglycerol, sodium sulfoxylate formal, or combinations thereof.

The process for preparing the formulation in accordance with an embodiment of this disclosure may comprise the step of adjusting the pH. pH may be adjusted by adding a pH adjusting agent. In an alternative embodiment the pH of the final formulation may be adjusted using acidic or basic solutions. For example, the pH of the final formulation may be adjusted to a value from about 4.0 to about 8.0, or from about 4.5 to about 7.5, preferably from about 5.0 to about 7.0. The preferred final pH of the formulation may be, for example, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9 or 7.0.

The processes in accordance with an embodiment of this disclosure may further comprise one or more sterilization steps. Sterilization may be accomplished by any suitable method, for example, heat sterilization, sterilization by filtration, sterilization by UV radiation, gamma sterilization, among others. The formulation or its components in accordance with an embodiment of this disclosure may be sterilized separately.

In even another aspect of an embodiment of this disclosure a method is provided for controlling the reproductive cycle and/or ovulation in a female mammal comprising administering a suitable dose of the formulation of an embodiment of this disclosure to said female mammal.

In even another aspect of an embodiment of this disclosure a method is provided for synchronizing ovulation in a group of female mammals comprising administering a suitable dose of the formulation of an embodiment of this disclosure to said female mammals.

In even another aspect of an embodiment of this disclosure a method is provided for promoting ovulation in female mammals comprising administering a suitable dose of the formulation of an embodiment of this disclosure to said female mammal.

In even another aspect of an embodiment of this disclosure a method is provided for increasing the likelihood that a female mammal gets pregnant comprising administering a suitable dose of the formulation of an embodiment of this disclosure to said female mammals. For example, the method may comprise a method for increasing the likelihood that a female mammal gets pregnant after natural or artificial insemination thereof, or after the embryo transference.

In even another aspect of an embodiment of this disclosure a method is provided for reducing the anestrous period in female mammals comprising administering a suitable dose of the formulation of an embodiment of this disclosure to said female mammal.

In the methods in accordance with an embodiment of this disclosure, a suitable dose of the formulation of an embodiment of this disclosure is administered, wherein the dose of hormone required may be modified depending on the characteristics of the animal to be treated. In another embodiment, a dose of the formulation of an embodiment of this disclosure is administered comprising from about 50 mg to about 500 mg of progesterone or an analogue or a salt thereof, more preferably from about 150 mg to about 350 mg of progesterone or an analogue or a salt thereof, or preferably from about 200 mg to about 300 mg of progesterone or an analogue or a salt thereof, for example, 240 mg of progesterone or an analogue or a salt thereof.

In the methods in accordance with an embodiment of this disclosure, the formulation of an embodiment of this disclosure may be administered by an injection or by different alternative routes. In addition, the formulations may be administered, for example, by a subcutaneous, intravenous, intraparenteral, intramuscular or intradermal injection. Preferably, the formulation is administered by intramuscular injection.

The methods in accordance with an embodiment of this disclosure may comprise administering the formulation of an embodiment of this disclosure to a group of female mammals in an artificial insemination program, for example, a fixed-time artificial insemination (FTAI) program or a heat detection insemination program, which increases the proportion of animals that get pregnant after insemination. In one embodiment, insemination may be carried out from about 9 to about 11 days after administration of the formulation, for example, insemination may take place about 9, about 10 or about 11 days after administration of the formulation.

The methods in accordance with an embodiment of this disclosure may optionally comprise the administration of estradiol benzoate. The administration of estradiol benzoate comprises, for example, a dose of up to about 3 mg of estradiol benzoate, for example, a dose from about 1 mg to about 3 mg of estradiol benzoate, preferably a dose of about 2 mg of estradiol benzoate. In other embodiments, it is possible to use any other suitable dose to cause atresia of the follicles existing at the beginning of the treatment and thus preventing the formation of persistent follicles that negatively interfere with fertility. The administration of estradiol benzoate may be carried out, for example, by instramuscular injection or by any other appropriate route of administration. The administration of estradiol benzoate is carried out, for example, the same day the formulation of an embodiment of this disclosure is administered. In another embodiment, the administration of estradiol benzoate may also be carried out one or more days before or one or more days after the administration of the formulation of an embodiment of this disclosure.

The methods in accordance with an embodiment of this disclosure may optionally comprise the administration of a prostaglandin or a prostaglandin analogue or a salt thereof, for example, d-cloprostenol acetate. The administration of prostaglandin may comprise, for example, a dose of up to about 0.500 mg of prostaglandin, for example, a dose from about 0.075 mg to about 0.500 mg of prostaglandin, preferably a dose of about 0.150 mg of prostaglandin. In other embodiments, it is possible to use any other suitable dose to generate a luteolytic action, achieving the decrease of the progesterone concentration in blood. The administration of prostaglandin may be carried out, for example, by intramuscular injection or by any other appropriate route of administration. The administration of prostaglandin may be carried out, for example, a few days before and/or a few days after administering the formulation of an embodiment of this disclosure, for example, from about 4 days before to 10 days after application of said formulation. The administration of prostaglandin may be carried out, for example, about 2 days before and/or about 7 to about 9 days after administration of said formulation. The administration of prostaglandin may be carried out for example, about 2 days before and/or about 7 days after the administration of said formulation, and/or about 8 days after the administration of said formulation.

The methods in accordance with an embodiment of this disclosure may optionally comprise the administration of gonadotropin-releasing hormone (GnRH), or an analogue or a salt thereof, for example, buserelin acetate. The administration of GnRH or an analogue or a salt thereof may comprise, for example, a dose of up to about 0.03 mg, or a dose from about 0.001 mg to about 0.03 mg, or a dose from about 0.005 mg to about 0.0150 mg, preferably a dose of about 0.0084 mg. In other embodiments, any other suitable dose may be used to control the synthesis and release of LH and FSH to help with the maturation and growth of the follicle to then produce the ovulation and formation of the corpus luteum. The administration of GnRH or an analogue or a salt thereof may be carried out, for example, by intramuscular injection or by any other appropriate route of administration. The administration of GnRH or an analogue or a salt thereof can be carried out, for example, some days after the formulation of an embodiment of this disclosure has been administered, for example, from about 9 and about 11 days after administration of the formulation for example, about 9, about 10 or about 11 days after administration of the formulation. In an artificial insemination program, the administration of GnRH or an analogue or a salt thereof may be carried out, for example, the same day of the insemination, or a different day, for example, one day before the day wherein the insemination is performed.

The methods in accordance with an embodiment of this disclosure may optionally comprise the administration of Equine Chorionic Gonadotropin (eCG) hormone. The administration of eCG may comprise, for example, a dose of up to about 1000 IU of eCG, or a dose of from about 400 IU to about 800 IU of eCG, or a dose of from about 300 IU to about 400 IU of eCG, preferably a dose of about 500 IU of eCG. In other embodiments, any other suitable alternative dose may be used to control the synthesis and release of FSH and LH to help with the maturation and growth of the follicle. The administration of eCG may be carried out, for example, by intramuscular injection or by any other appropriate route of administration. The administration of eCG may be carried out, for example, some days after the formulation of an embodiment of this disclosure has been administered, for example, from about 6 to about 8 days after the administration of the formulation, for example, about 6, about 7 or about 8 days after the administration of the formulation.

The methods in accordance with an embodiment of this disclosure may optionally comprise the administration of estradiol cypionate or an analogue thereof. The administration of estradiol cypionate may comprise, for example, a dose of up to about 1 mg of estradiol cypionate, preferably a dose of about 0.5 mg of estradiol cypionate. In other embodiments, any other suitable dose may be used to generate a preovulatory LH surge and prepare mature follicles to ovulate. The administration of estradiol cypionate may be carried out, for example, by intramuscular injection or by any other appropriate route of administration. The administration of estradiol cypionate may be carried out, for example, some days after the formulation of an embodiment of this disclosure has been administered, for example, from about 7 to about 8 days after the administration of said formulation, for example, about 7 after the administration of said formulation, or about 8 days after the administration of said formulation. In a method in accordance with an embodiment of this disclosure, if the method comprises administering prostaglandin, the administration of estradiol cypionate may be carried out, for example, the same day of administration of prostaglandin.

The methods in accordance with an embodiment of this disclosure are primarily adapted for use in cattle, but may be modified in order to adapt them to any female mammal, for example, other domestic or farm animal. In other embodiments, said female mammal may be pigs, goats, sheep, horses, camels, among others.

The methods in accordance with an embodiment of this disclosure may comprise, for example, without limitation, the protocols described below. The insemination step is optional and is included in the methods that aim to increase the likelihood that the female mammal gets pregnant after the insemination. Timing of insemination may be predetermined by knowing the pre-ovulation times, which can be detected by ultrasonography or by manifestation of heat.

Protocol 1

Day 0: Administration of the formulation of an embodiment of this disclosure. Administration of estradiol benzoate.

Day 7: Administration of prostaglandin.

Day 9: Administration of gonadotropin releasing hormone (GnRH).

Day 10: Insemination.

Protocol 2

Day 0: Administration of the formulation of an embodiment of this disclosure. Administration of estradiol benzoate.

Day 7: Administration of prostaglandin.

Day 9: Administration of gonadotropin releasing hormone (GnRH). Insemination.

Protocol 3

Day 0: Administration of the formulation of an embodiment of this disclosure. Administration of estradiol benzoate.

Day 8: Administration of prostaglandin. Administration of estradiol cypionate.

Day 10: Administration of gonadotropin releasing hormone (GnRH). Insemination.

Protocol 4

Day 0: Administration of the formulation of an embodiment of this disclosure. Administration of estradiol benzoate.

Day 8: Administration of prostaglandin.

Day 10: Administration of gonadotropin releasing hormone (GnRH).

Day 11: Insemination.

Protocol 5
Day 0: Administration of the formulation of an embodiment of this disclosure. Administration of estradiol benzoate.
Day 8: Administration of prostaglandin. Administration of estradiol cypionate.
Day 11: Insemination.

Protocol 6
Day 0: Administration of the formulation of an embodiment of this disclosure. Administration of estradiol benzoate.
Day 7: Administration of prostaglandin. Administration of estradiol cypionate.
Day 9: Administration of gonadotropin releasing hormone (GnRH).
Day 10: Insemination.

Protocol 7
Day 0: Administration of the formulation of an embodiment of this disclosure. Administration of estradiol benzoate.
Day 8: Administration of prostaglandin. Administration of equine chorionic gonadotropin (eCG)
Day 9: Administration of estradiol benzoate.
Day 10 (68 hours after administration of prostaglandin): Insemination.

Protocol 8
Day 0: Administration of the formulation of an embodiment of this disclosure. Administration of estradiol benzoate.
Day 6: Administration of prostaglandin.
Day 9 (68-72 hours after administration of prostaglandin): Insemination.

Protocol 9
Day 0: Administration of the formulation of an embodiment of this disclosure. Administration of estradiol benzoate.
Day 7 (in the morning): Administration of prostaglandin.
Day 8 (in the morning): Administration of estradiol benzoate.
Day 9 (68-72 hours after administration of prostaglandin): Fixed-time insemination.

Protocol 10
Day 0: Artificial Insemination.
Day 13: Administration of the formulation of an embodiment of this disclosure.
Day 21-25: Insemination at detected heat.

Protocol 11
Day 0: Administration of the formulation of an embodiment of this disclosure.
Day 23: Administration of gonadotropin releasing hormone (GnRH).
Day 30: Administration of prostaglandin.
Day 30+52 hours: Detection of heat.
Day 33: Administration of gonadotropin releasing hormone (GnRH). Insemination.

Protocol 12
Day 0: Administration of the formulation of an embodiment of this disclosure. Administration of gonadotropin releasing hormone (GnRH).
Day 5: Administration of prostaglandin and repetition of dose at 12 hours.
Day 5+52 hours: Detection of heat.
Day 8: Administration of gonadotropin releasing hormone (GnRH). Insemination.

Protocol 13
Day 0: Administration of the formulation of an embodiment of this disclosure. Administration of gonadotropin releasing hormone (GnRH).
Day 7: Administration of prostaglandin.
Day 7-13: Detection of heat. Insemination.

Protocol 14
Day 0: Administration of the formulation of an embodiment of this disclosure. Administration of gonadotropin releasing hormone (GnRH).
Day 7 (in the morning): Administration of prostaglandin.
Day 7+72-84 hours: Detection of heat.
Day 10: Administration of gonadotropin releasing hormone (GnRH). Insemination.

Protocol 15
Day 0: Administration of prostaglandin.
Day 0-3: Detection of estrus. Insemination.
Day 3: Administration of the formulation of an embodiment of this disclosure. Administration of gonadotropin releasing hormone (GnRH).
Day 9: Administration of prostaglandin.
Day 9-12: Detection of heat. Insemination.

Protocol 16
Day 0: Administration of prostaglandin.
Day 0-3: Detection of heat. Insemination.
Day 3: Administration of the formulation of an embodiment of this disclosure. Administration of gonadotropin releasing hormone (GnRH).
Day 9: Administration of prostaglandin.
Day 12: Administration of gonadotropin releasing hormone (GnRH). Insemination.

Protocol 17
Day 0: Administration of prostaglandin.
Day 14: Administration of prostaglandin.
Day 28: Administration of the formulation of an embodiment of this disclosure. Administration of gonadotropin releasing hormone (GnRH).
Day 35: Administration of prostaglandin.
Day 37: Administration of gonadotropin releasing hormone (GnRH).
Day 38: Fixed-time insemination.

Protocol 18
Day 0: Administration of the formulation of an embodiment of this disclosure. Administration of estradiol benzoate.
Day 6: Administration of prostaglandin. Administration of equine chorionic gonadotropin (eCG)
Day 9 (72 hours post prostaglandin): Administration of gonadotropin releasing hormone (GnRH). Fixed-time insemination.

The administration times and doses of the formulation of an embodiment of this disclosure as well as the administration times and doses of each hormone of the methods described above may be modified depending on the characteristics of the animal or group of animals to be treated.

EXAMPLES

Example 1: Formulations

Some non-limiting examples of formulations of an embodiment of the present disclosure that were prepared and assayed comprise the compounds and concentrations as indicated in the following tables.

Formulation 1

| Components | Concentration (mg/mL) |
|---|---|
| Progesterone | 47 |
| Benzyl alcohol | 40 |
| Benzyl benzoate | 23 |
| Ethanol | 118 |
| Stearic Acid | 24 |
| Hydroxyethyl cellulose | 4 |
| Ethoxylated castor oil, at 40 moles of ethylene oxide | 99 |
| Poloxamer P407 | 69 |
| Refined sesame oil | 17 |
| Water | 559 |

Formulation 2

| Components | Concentration (mg/mL) |
|---|---|
| Progesterone | 47 |
| Benzyl alcohol | 38 |
| Benzyl benzoate | 22 |
| Ethanol | 118 |
| Stearic Acid | 24 |
| Hydroxyethyl cellulose | 3.5 |
| Ethoxylated castor oil, at 40 moles of ethylene oxide | 64 |
| Poloxamer P407 | 69 |
| Refined sesame oil | 16 |
| d-α-tocopherol propylene glycol 1000 succinate | 5 |
| Xanthan gum | 0.1 |
| Water | 599 |

Formulation 3

| Components | Concentration (mg/mL) |
|---|---|
| Progesterone | 50 |
| Benzyl alcohol | 40 |
| Benzyl benzoate | 20 |
| Ethanol | 120 |
| Stearic Acid | 20 |
| Hydroxyethyl cellulose | 4 |
| Ethoxylated castor oil, at 40 moles of ethylene oxide | 60 |
| Poloxamer P407 | 70 |
| Refined sesame oil | 20 |
| d-α-tocopherol propylene glycol 1000 succinate | 5 |
| BHA | 1 |
| BHT | 1 |
| Gum Arabic | 1 |
| Xanthan gum | 0.1 |
| Water | 600 |

Formulation 4

| Components | Concentration (mg/mL) |
|---|---|
| Progesterone | 50 |
| Benzyl alcohol | 40 |
| Benzyl benzoate | 20 |
| Ethanol | 120 |
| Stearic Acid | 20 |
| Hydroxyethyl cellulose | 4 |
| Ethoxylated castor oil, at 40 moles of ethylene oxide | 60 |
| Poloxamer P407 | 70 |
| Refined sesame oil | 20 |
| d-α-tocopherol propylene glycol 1000 succinate | 5 |
| BHA | 1 |
| Gum Arabic | 1 |
| Water | 600 |

Formulation 5

| Components | Concentration (mg/mL) |
|---|---|
| Progesterone | 50 |
| Benzyl alcohol | 40 |
| Benzyl benzoate | 20 |
| Ethanol | 120 |
| Stearic Acid | 20 |
| Hydroxyethyl cellulose | 4 |
| Ethoxylated castor oil, at 40 moles of ethylene oxide | 60 |
| Kolliphor P407 | 70 |
| Refined sesame oil | 20 |
| d-α-tocopherol propylene glycol 1000 succinate | 5 |
| BHT | 2 |
| Water | 600 |

Formulation 6

| Components | Concentration (mg/mL) |
|---|---|
| Progesterone | 47.1 |
| Benzyl alcohol | 53.3 |
| Benzyl benzoate | 21.9 |
| Ethanol | 118 |
| Stearic Acid | 23.6 |
| Hydroxyethyl cellulose | 3.6 |
| Ethoxylated castor oil, at 40 moles of ethylene oxide | 100 |
| Poloxamer P407 | 63.9 |
| Water | 556.7 |

Formulation 7

| Components | Concentration (mg/mL) |
|---|---|
| Progesterone | 47.1 |
| Benzyl alcohol | 37.6 |
| Benzyl benzoate | 21.9 |
| Ethanol | 118 |
| Stearic Acid | 23.6 |
| Ethoxylated castor oil, at 40 moles of ethylene oxide | 100 |
| Poloxamer P407 | 63.9 |
| Refined sesame oil | 15.7 |
| Water | 566 |

Example 2: Process for Preparing an Injectable Formulation

The process described below is an example of how to prepare one of the injectable formulations of an embodiment of the present disclosure (Formulation 1 of Example 1).

The process for preparing the injectable formulation of the present disclosure consists, firstly, of preparing five pre-products A-E. The processes for the preparation of these pre-products are described below.

Preparation of Pre-Product A Ethoxylated castor oil, at 40 moles of ethylene oxide, is dissolved in distilled water at a temperature of 70° C. to a concentration of about 30% by weight (m/m). Dissolution is carried out with slow stirring for 5 minutes or until complete dissolution. This pre-product may be stored at 4° C. until further use.

Preparation of Pre Product B

Firstly, stearic acid is added to a vessel containing ethanol at a temperature of 60° C., and stirred using a magnetic stirrer until complete dissolution. Next, progesterone is added and stirring is continued until its complete dissolution. Final concentrations of stearic acid and progesterone comprise about 14% by weight (m/m).

Preparation of Pre-Product C

Poloxamer P407, for example, Kolliphor® P407, is added to distilled water at a temperature of about 70° C. to a concentration of about 25% by weight (m/m). The mixture is stirred continuously for a period of time. Then, the mixture is stored at a temperature of 4° C. until a clear and homogeneous liquid is formed.

Preparation of Pre-Product D

In the first place, a mixture of benzyl alcohol, benzyl benzoate, and ethanol is prepared. To this mixture progesterone is added and the mixture is stirred to its complete dissolution. Finally, refined sesame oil is included and stirred until a homogeneous mixture is obtained. The final half-finished product contains about 38% by weight (m/m) benzyl alcohol, about 22% by weight (m/m) benzyl benzoate, about 0.3% by weight (m/m) ethanol, about 16% by weight (m/m) sesame oil and about 24% by weight (m/m) progesterone. This pre-product may be stored at 4° C. until further use.

Preparation of Pre-Product E

Hydroxyethyl cellulose (HEC) is dissolved in distilled water at a temperature of 70° C. to a final concentration of about 3% by weight (m/m) HEC. Then, the solution is slowly stirred until a homogeneous gel is formed. This pre-product may be stored at 4° C. until further use.

Final Preparation

Once pre-products A-E are ready, preparation of the final formulation is carried out.

For example, for preparing 5000 mg of formulation 1 of Example 1, firstly about 850 mg of pre-product B are mixed with about 1400 mg of pre-product C. Then, about 1650 mg of pre-product A and about 500 mg of pre-product D are added to this suspension. Finally, about 600 mg of pre-product E are added.

Example 3: Treatment Protocols

Preliminary Considerations

First, for the treatment protocols as described in the following assays, bovine animals were selected according to the criteria outlined below. This selection was made in order to work with cows that are suitable for a heat synchronization.

Cows having reached sexual maturity were selected, that is, those of more than about 15 months of age and weighing more than about 260 kilograms.

Regarding their body condition, preferably those animals scoring from about 2.5 to 3.5 points on a scale of 5 as described by Lowman et al., (*The East of Scotland College of Agriculture; Edinburgh;* 1976; pp. 1-31 (Vol. 6) were selected.

The assessment by this scale is not exclusive since there were cases in which scoring was met but the animals were not fit for other reasons, for example, cows in anestrous phase. Furthermore, some animals which did not achieve the preferred scoring, for example, animals lacking weight but which were in a state of weight gaining, were selected. Moreover, animals with a preferred scoring, but having malformations which might prevent the animal from feeding correctly, for example, animals with crooked jaws, were discarded.

Another aspect considered for selecting animals was their state of health.

For example, cows showing purulent vaginal discharge caused by infections such as vaginitis, erratic behavior, wobbling, or sadness caused by internal or external parasites, lack or significant wear of teeth and cows with any other type of pathology, were discarded.

Further, the nutritional state was assessed in a feeding history study of the last month to establish weight gain of the cows to be selected.

Finally, an ultrasound was performed in all preselected animals and those cows having a size of corpus luteum or follicles equal or greater than 8 mm were selected. Cows with small ovaries, small follicles (indicative of anestrus), and pregnant cows were discarded.

Protocols

The protocols comprising administering the formulation of an embodiment of the present disclosure were adapted for use in cattle but may be modified as needed for use in other animals. Further, the assessed doses and application times may vary depending on the type of animal and other factors. The following protocols were tested:

Protocol A

Day 0 (in the morning):

Application of intramuscular injection of the formulation of an embodiment of the present disclosure at a dose of 240 mg progesterone.

Application of intramuscular injection of 2 mg estradiol benzoate.

Day 7 (in the morning):

Application of an intramuscular injection of 0.150 mg d-cloprostenol acetate.

Day 9 (in the morning):

Application of intramuscular injection of 0.0084 mg buserelin.

Day 10 (in the morning):

Insemination.

Protocol B

Day 0 (in the morning):

Application of intramuscular injection of the formulation of an embodiment of the present disclosure at a dose of 240 mg progesterone.

Application of intramuscular injection of 2 mg estradiol benzoate.

Day 7 (in the morning):

Application of an intramuscular injection of 0.150 mg d-cloprostenol acetate.

Day 9 (in the morning):

Application of intramuscular injection of 0.0084 mg buserelin.

Insemination.

Protocol B1

Day 0 (in the morning):

Insertion of a Bovine Intravaginal Device (DIB) with 1 g progesterone.

Application of intramuscular injection of 2 mg estradiol benzoate.

Day 7 (in the morning):

Application of an intramuscular injection of 0.150 mg d-cloprostenol acetate.

Removal of DIB.

Day 9 (in the morning):
Application of intramuscular injection of 0.0084 mg buserelin.
Insemination.
Protocol C
Day 0 (in the morning):
Application of intramuscular injection of the formulation of an embodiment of the present disclosure at a dose of 240 mg progesterone.
Application of intramuscular injection of 2 mg estradiol benzoate.
Day 8 (in the morning):
Application of an intramuscular injection of 0.150 mg d-cloprostenol acetate.
Application of intramuscular injection of 0.5 mg estradiol cypionate
Day 10 (in the morning):
Application of intramuscular injection of 0.0084 mg buserelin.
Insemination.
Protocol D
Day 0 (in the morning):
Application of intramuscular injection of the formulation of an embodiment of the present disclosure at a dose of 240 mg progesterone.
Application of intramuscular injection of 2 mg estradiol benzoate.
Day 8 (in the morning):
Application of an intramuscular injection of 0.150 mg d-cloprostenol acetate.
Day 10 (in the morning):
Application of intramuscular injection of 0.0084 mg buserelin.
Day 11 (in the morning):
Insemination.
Protocol E
Day 0 (in the morning):
Application of intramuscular injection of the formulation of an embodiment of the present disclosure at a dose of 240 mg progesterone.
Application of intramuscular injection of 2 mg estradiol benzoate.
Day 8 (in the morning):
Application of an intramuscular injection of 0.150 mg d-cloprostenol acetate.
Application of intramuscular injection of 0.5 mg estradiol cypionate
Day 11 (in the morning):
Insemination.
Protocol E1
Day 0 (in the morning):
Insertion of a Bovine Intravaginal Device (DIB) with 0.5 g progesterone.
Application of intramuscular injection of 2 mg estradiol benzoate.
Day 8 (in the morning):
Application of an intramuscular injection of 0.150 mg d-cloprostenol acetate.
Application of intramuscular injection of 0.5 mg estradiol cypionate
Removal of DIB.
Day 10 (in the morning):
Insemination.
Protocol F
Day 0 (in the morning):
Insertion of a Bovine Intravaginal Device (DIB) with 0.5 g progesterone.
Application of intramuscular injection of 2 mg estradiol benzoate.
Day 7 (in the morning):
Application of an intramuscular injection of 0.150 mg d-cloprostenol acetate.
Application of intramuscular injection of 0.5 mg estradiol cypionate
Removal of DIB.
Day 9 (in the morning):
Insemination.
Protocol F1
Day 0 (in the morning):
Insertion of a Bovine Intravaginal Device (DIB) with 1 g progesterone.
Application of intramuscular injection of 2 mg estradiol benzoate.
Day 7 (in the morning):
Application of an intramuscular injection of 0.150 mg d-cloprostenol acetate.
Removal of DIB.
Day 9 (in the morning):
Insemination.
Application of intramuscular injection of 0.0084 mg buserelin.
In the case of heifers, the dose of the formulation of the present disclosure may be replaced by 192 g progesterone.

Example 4: Blood Progesterone Levels

Cows of the following breeds were selected: Holando-Argentino (argentine dairy breed), Brangus (synthetic breed derived by crossing a British breed, such as Aberdeen Angus, with a cow of the Brahman breed at a relationship of ⅜, a crossing designated zebuine) and Aberdeen Angus, according to the criteria outlined in Example 3.

Approximately 15 animals of each breed were selected and treated with the formulation of an embodiment of the present disclosure (Formulation 1 of Example 1) as described in Protocol A. In all cases, 0.150 mg d-cloprostenol acetate were applied two days before starting the treatment protocol in order to lyse the corpus luteus and allow for baseline progesterone on day 0.

Blood extractions were performed from all animals as from two days before starting the treatment protocol. Then, blood extractions were conducted periodically up to day 14 after starting the treatment.

Approximately 8 to 10 mL of venous blood were extracted preferably from the jugular vein or from the coccygeal vein, after previous cleaning of the extraction zone with 70% v/v ethanol or 10% v/v povidone-iodine solution. Blood was collected in 5 mL sterile tubes and left to stand at room temperature for 2 to 3 hours until clotting had occurred. Then it was centrifuged at 45000 rpm for 15 minutes to extract the serum. Finally, 2 aliquots of 1.5 mL serum were taken and deposited in 5 mL test tubes. These tubes may be stored at −18° C. for further analysis.

Serum samples were analyzed to measure progesterone levels using the Immulite 2000 system (DPC/Siemens).

The results obtained for the different groups of cows are summarized in the following tables. Average values of progesterone concentration in the blood from each group of animals are represented.

The results shown in the following Tables 1 to 3 are also represented in FIG. 1.

TABLE 1

| Holando-Argentino | |
|---|---|
| Day | [P4] ng/mL |
| −2 | 8.30 |
| 0 | 0.37 |
| 2 | 2.20 |
| 4 | 3.10 |
| 6 | 7.42 |
| 7 | 5.00 |
| 8 | 3.14 |
| 9 | 0.9 |
| 10 | 0.70 |
| 12 | 2.10 |
| 14 | 3.80 |

TABLE 2

| Brangus | |
|---|---|
| Day | [P4] ng/mL |
| −2 | 7.42 |
| 0 | 3.00 |
| 2 | 1.31 |
| 4 | 2.3 |
| 5 | 3.90 |
| 7 | 2.74 |
| 9 | 1.10 |
| 10 | 0.80 |
| 12 | 0.76 |
| 14 | 3.40 |

TABLE 3

| Aberdeen Angus | |
|---|---|
| Day | [P4] ng/mL |
| −2 | 3.00 |
| 0 | 0.80 |
| 2 | 2.20 |
| 4 | 2.30 |
| 5 | 4.20 |
| 7 | 1.18 |
| 9 | 0.60 |
| 10 | 0.57 |
| 12 | 2.80 |
| 14 | 4.00 |

As may be observed from the above results, the formulation of an embodiment of the present disclosure allows for a delayed release of progesterone into the blood stream, thus generating a sustained concentration of said hormone about 5 to 7 days after starting the treatment protocol when there is a pronounced reduction of progesterone concentration.

The results obtained in the present example show that the product an embodiment of the present disclosure defines a characteristic curve while maintaining the values required for a correct follicular growth. It should be noted that by the end of the treatment, i.e., after about 7 or 8 days, there is a reduction in progesterone levels, simulating what occurs with the removal of an intravaginal or implantable device. In other words, kinetics shown in FIG. 1 shows that by that time most of the injected progesterone has been consumed, which is a requirement to achieve ovulation.

Example 5: Ovulation and Follicular Dynamics

Example 5A

Cows of Holando-Argentino, Brangus and Aberdeen Angus breeds were selected according to the criteria outlined in Example 3.

About 30 animals of each breed were selected and divided into two groups. A group of each breed was treated with the formulation of an embodiment of the present disclosure (Formulation 1 of Example 1) as described in Protocol A. The other group was treated using an intravaginal device as described in Protocol F (Brangus and Aberdeen Angus breeds) or in Protocol F1 (Holando-Argentino breed). In all cases, 0.150 mg d-cloprostenol acetate were applied two days before starting the treatment protocol in order to lyse the corpus luteus and allow for baseline progesterone on day 0.

In order to monitor follicular dynamics in treated animals, scanning by transrectal ultrasound was performed using a DP-10 (Mindray Medical International Ltd.) of 6 to 8.5 Mhz with a lineal transducer. Ultrasounds were carried out on treatment days 0, 2, 4, 6, 7, 8, 9, 10 and 11 at the times indicated in the following table:

TABLE 4

| Days and times of ultrasound. | | | | | | | | | |
|---|---|---|---|---|---|---|---|---|---|
| | Day | | | | | | | | |
| Time | 0 | 2 | 4 | 6 | 7 | 8 | 9 | 10 | 11 |
| 8:00 am | X | X | X | X | X | X | X | X | X |
| 12:00 pm | | | | | | | X | X | X | X |
| 4:00 pm | | | | X | X | X | X | X | |
| 8:00 pm | | | | | | X | X | X | |

The results of ultrasounds for each group of the selected animals are summarized below and shown in Tables 5 to 7.

The results of the present example demonstrate that the formulation of an embodiment of the present disclosure provides an increase in the ovulation percentage. As may be seen in Table 5, a treatment with the formulation of an embodiment of the present disclosure produced higher ovulation percentages than a treatment with an intravaginal device in the three analyzed breeds. In addition, a greater average size of ovulatory follicles was observed (Table 6). Another important advantage when using the formulation of an embodiment of the present disclosure was that an improved synchronization of ovulation time as compared to the results obtained with the protocol using an intravaginal device was observed (Table 7). Most of the animals treated with the protocol including the formulation of an embodiment of the present disclosure ovulated during day 10 (that is, after 10 days of administering the formulation) in the afternoon. In contrast, when a treatment with an intravaginal device was used, ovulation times were more variable.

TABLE 5

| Ovulation percentage | | |
|---|---|---|
| Breed | Formulation 1 | DIB |
| Holando-Argentino | 100% | 56% |
| Brangus | 93% | 61% |
| Aberdeen Angus | 100% | 60% |

TABLE 6

Average size of ovulatory follicles

| Breed | Formulation 1 | DIB |
|---|---|---|
| Holando-Argentino | 17-18 mm | 16 mm |
| Brangus | 16 mm | 15 mm |
| Aberdeen Angus | 16 mm | 14 mm |

TABLE 7

Ovulation times

| Day/Time of ovulation | Formulation 1 | DIB |
|---|---|---|
| Holando-Argentina breed | | |
| Day 9, in the afternoon | 0% | 31% |
| Day 10, in the morning | 0% | 12.5% |
| Day 10, in the afternoon | 100% | 12.5% |
| No ovulation | 0% | 44% |
| Brangus breed | | |
| Day 9, in the afternoon | 0% | 27% |
| Day 10, in the morning | 0% | 27% |
| Day 10, in the afternoon | 86% | 7% |
| Day 11, in the morning | 7% | 0% |
| No ovulation | 7% | 39% |
| Aberdeen Angus breed | | |
| Day 9, in the afternoon | 0% | 40% |
| Day 10, in the morning | 0% | 27% |
| Day 10, in the afternoon | 100% | 0% |
| No ovulation | 0% | 33% |

Figure 2A:
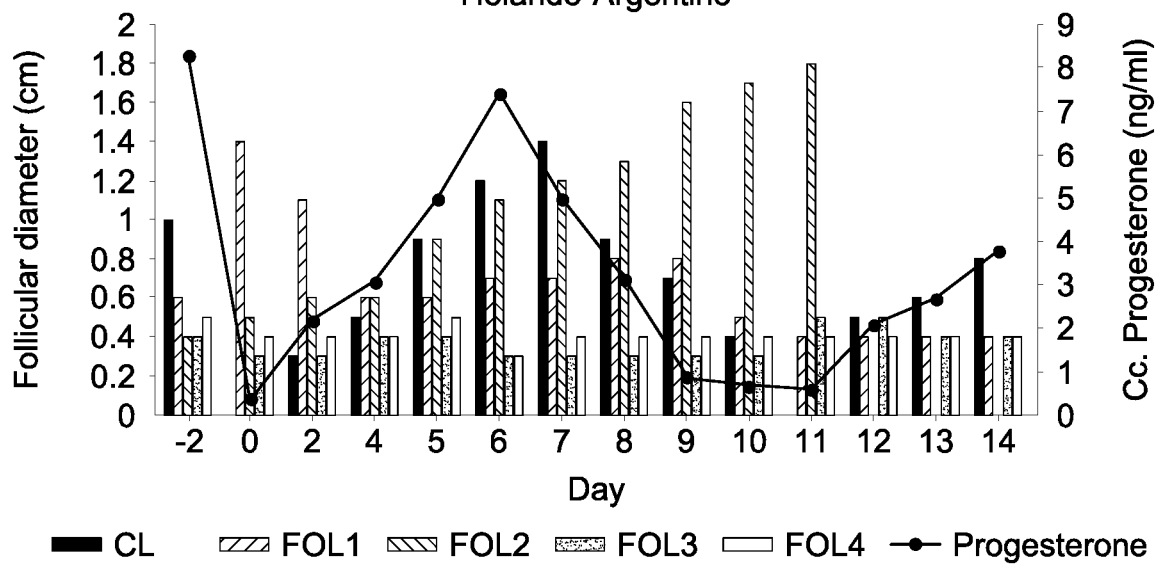
FIGS. 2A through 2C show graphics comparing follicular growth (cm) with variable blood progesterone (ng/mL), as a function of treatment days, for the three evaluated cows (A: Holando-Argentina, B: Brangus, and C: Aberdeen Angus). The most representative follicles were evaluated (FOL 1, 2, 3, and 4), i.e., follicles having an appropriate size for carrying out the measurement. Further represented is the size of the corpus luteum (CL).
Figure 2B:
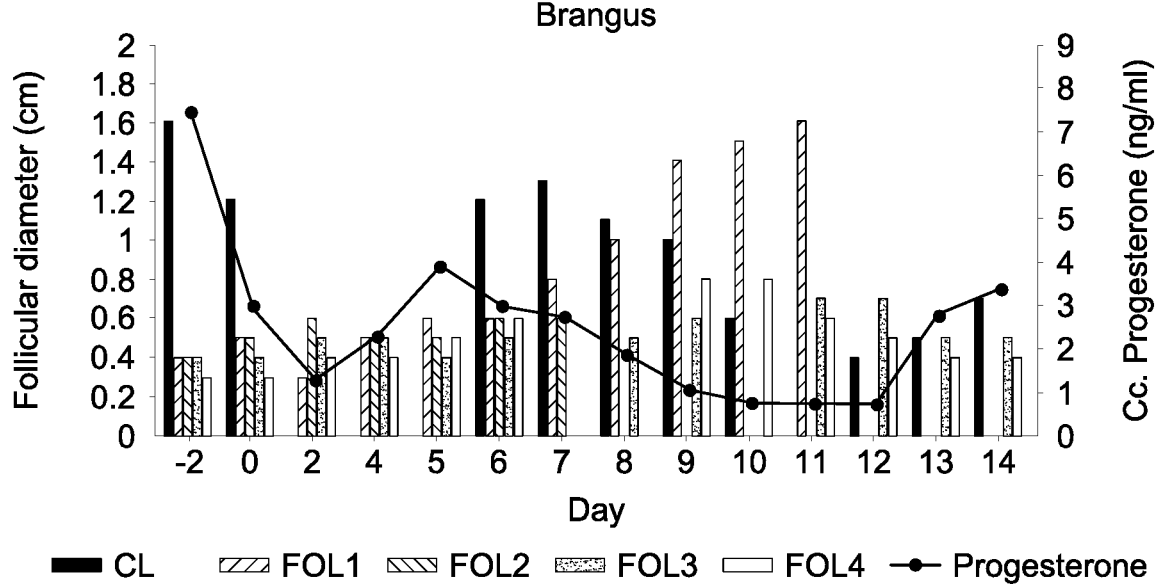
Figure 2C:
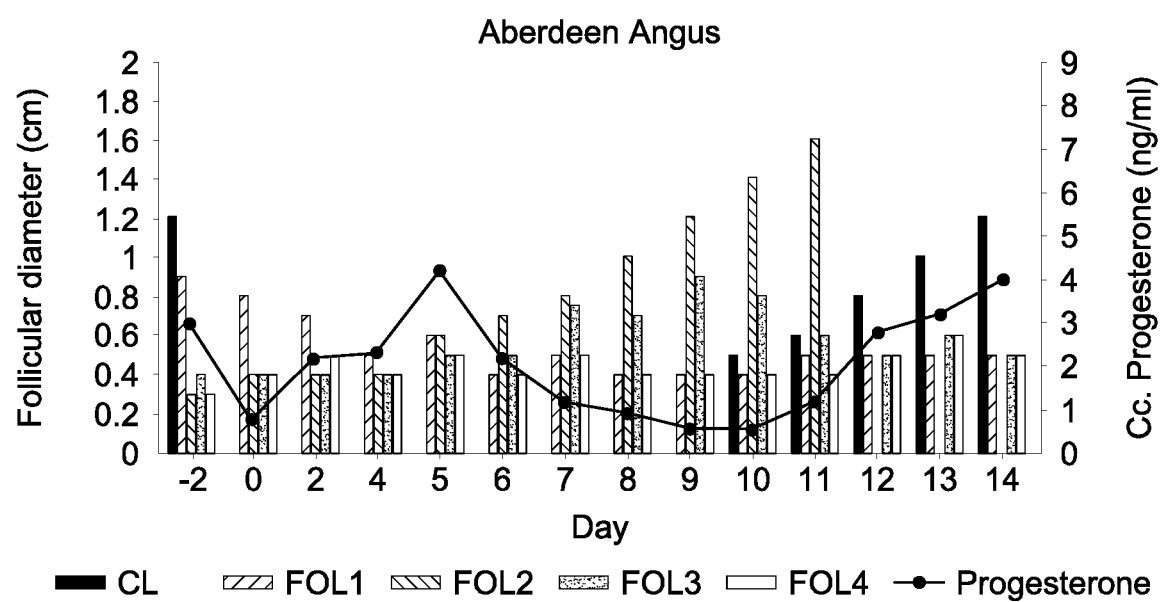

Further, the results shown in FIG. 2 demonstrate that follicular growth is accompanied by a sustained release of progesterone. Progesterone concentration in blood increases gradually from the first through the sixth day inclusive (or fifth in some cases), followed by development of a follicle that differ in size as from the fifth day, to continue its growth until ovulation (end of day 10). From day 7 on it is observed that progesterone concentration begins to decrease until it reaches baseline levels by days 9-10, in agreement with the above-mentioned follicular growth. These results are key to achieve the desired benefits, since not only is progesterone release maintained during the entire treatment, but it is also consumed by the end thereof, simulating the removal of an intravaginal device and allowing for correct follicle maturation until ovulation.

Ovulation percentages obtained by using the formulation of an embodiment of the present disclosure (about 100%) and enhanced synchronization of ovulation times are unexpected advantages as compared to intravaginal devices.

Example 5B

A comparative assay was also performed to assess the ovulation percentages using formulations 1, 6 and 7 described in Example 1.

For this assay, Aberdeen Angus cows without calves at foot were used.

A minimum of three animals were treated with each one of formulations 1, 6 and 7, using the Protocol A described in Example 3. The results are shown in Table 8 below.

TABLE 8

Ovulation percentage

| Fromulation # | Ovulation % |
|---|---|
| 1 | 100% |
| 6 | 66% |
| 7 | 100% |

The results show that the three assayed formulations produced acceptable ovulation percentages (about ⅔ of the animals).

Example 6. Pregnancy Percentage

Milking Yard Cows

Cows of the Holando-Argentina breed were selected according to the criteria set out in Example 3, with the addition that all treated cows have had at least one calving and are producing milk.

Nine batches of about 30 animals each were selected and each batch was divided into two groups. One group of each batch was treated with the formulation of an embodiment of the present disclosure (Formulation 1 of Example 1) as described in Protocol A and the other group was treated with an intravaginal device following Protocol B1.

Pregnancy of animals treated during days 35 to 45 after starting the treatment was evaluated. Determination was carried out by ultrasound. The results thus obtained are shown in Table 9 below.

TABLE 9

Pregnancy percentage

| | Percentage of pregnant cows | |
|---|---|---|
| Batch No. | Formulation 1 | DIB |
| 1 | 75% | 33% |
| 2 | 47% | 38% |
| 3 | 81% | 31% |
| 4 | 62% | 42% |
| 5 | 71% | 38% |
| 6 | 68% | 51% |
| 7 | 65% | 49% |
| 8 | 53% | 42% |
| 9 | 75% | 37% |
| Cumulative | 67% | 40% |

In addition, cows of the Holando-Argentina breed were selected according to the criteria set out in Example 3, except that the treated cows were only heifers.

Forty five animals were selected and divided into two groups. One group of each batch was treated with the formulation of an embodiment of the present disclosure (Formulation 1 of Example 1) as described in Protocol A and the other group was treated with an intravaginal device following Protocol F.

Pregnancy of animals treated during days 35 to 45 after starting the treatment was evaluated. Determination was carried out by ultrasound. The results thus obtained are shown in Table 10 below.

TABLE 10

Pregnancy percentage of Holando-Argentina heifers
Percentage of pregnant cows

| Formulation 1 | DIB |
|---|---|
| 77% | 63% |

Meat Cows

Fifty six cows of the Aberdeen Angus breed were selected according to the criteria set out in Example 3 and separated into two batches. The first batch comprised 30 cows which were treated with the formulation of an embodiment of the present disclosure (Formulation 1 of Example 1) as described in Protocol E and the second batch of 26 animals was treated with an intravaginal device as described in Protocol E1.

Pregnancy of animals treated during days 35 to 45 after starting the treatment was evaluated by ultrasound.

It was noted that 21 out of the 30 cows treated with the formulation of an embodiment of the present disclosure became pregnant before 45 days after starting the treatment, that is, a pregnancy percentage of 70% was obtained. On the other hand, only 14 out of the 26 cows treated with the intravaginal device became pregnant before 45 days after starting the treatment, that is, a pregnancy percentage of 54%.

The above assay was repeated in 60 animals with the difference that in this case insemination was carried out with sexed semen. A first group of 40 animals was treated with the formulation of an embodiment of the present disclosure (Formulation 1 of Example 1) as described in Protocol E and the second group of 20 animals was treated with an intravaginal device as described in Protocol E1.

It was noted that 24 out of the 40 cows treated with the formulation of the present disclosure (Protocol E) became pregnant before 45 days after starting the treatment, that is, a pregnancy percentage of 58% was obtained. On the other hand, only 7 out of the 20 cows treated with the intravaginal device (Protocol E1) became pregnant before 45 days after starting the treatment, that is, a pregnancy percentage of 35%.

The above results are summarized in Table 11.

TABLE 11

Pregnancy percentage for meat cows

| | Percentage of pregnant cows | |
|---|---|---|
| | Formulation 1 | DIB |
| Non-sexed semen | 70% | 54% |
| Sexed semen | 58% | 35% |

In the above-described assays of this example, both for milking yard cows as for meat cows, the pregnancy percentages achieved were higher when the formulation of an embodiment of the present disclosure is used as compared to the use of intravaginal devices. These results show that the treatments comprising administration of the formulation of an embodiment of the present disclosure increase the likelihood of pregnancy in an animal, as compared to the treatments with intravaginal devices. It should be noted that these results were consistent with the high rate and ovulation synchronization obtained with all assessed breeds, as observed in Example 5.

NON-PATENT REFERENCES

1. N. Ahmad, F. N. Schrick, R. L. Butcher, E. K. Inskeep. Effect of persistent follicles on early embryonic losses in beef cows. Biol. Reprod. 52 (1995) 1129-1135.
2. Beck, L. R., Cowsar, D. R., Lewis, D. H., Cosgrove Jr, R. J., Riddle, C. T., Lowry, S. L., & Epperly, T. (1979). A new long-acting injectable microcapsule system for the administration of progesterone. Fertility and sterility, 31(5), 545-551.
3. S. Burggraaf, M. J. Rathbone, C. R. Bunt, C. R. Burke, K. L. Pickering. Effect of Shore hardness, inert fillers and progesterone particle size upon the reléase of progesterone from a controlled reléase intravaginal drug delivery system. Proc. Int. Symp. Control. Rei. Bioact. Mater. 24 (1997) 147-148. 95.
4. C. R. Bunt, M. J. Rathbone, S. Burggraaf, C. Ogle. Development of a QC reléase assessment method for a physically large veterinary product containing a highly water insoluble drug and the effect of formulation variables upon reléase. Proc. Int. Symp. Control. Rei. Bioact. Mater. 24 (1997) 145-146.
5. C. R. Burke, M. Mihm, K. L. Macmillan, J. F. Roche. Some effects of prematurely elevated concentrations of progesterone on luteal and follicular characteristics during the oestrus cycle in heifers. Anim. Reprod. Sci. 35 (1994) 27-39.
6. C. R. Burke, S. Burggraaf, C. R. Bunt, M J. Rathbone, K. L. Macmillan. Use of pregnant dairy cows in product development of the intravaginal progesterone releasing (CIDR) device. Proc. NZ Soc. Anim. Prod., 57 (1997).
7. M. J. Carrick, J. N. Shelton. The synchronisation of oestrus in cattle with progestogen impregnated intravaginal sponges. J. Reprod. Fértil. 14 (1967) 21-32.
8. S. E. Curl, W. Durfey, R. Patterson, D. W. Zinn. Synchronization of estrus in cattle with subcutaneous implants. J. Anim. Sci. 27 (1968) 1189.
9. S. R. Davis, R. A. S. Welch, M. G. Pierce, A. J. Peterson. Induction of lactation in nonpregnant cows by oestradiol 17b and progesterone from an intravaginal sponge. J. Dairy Sci. 66 (1983) 450^157.
10. G. F. Duirs, K. L. Macmillan, D. G. McCall, W. H. McMillan, A. M. Day. CIDR systems in suckling beef cows. Proc. Aust. Soc. Reprod. Biol. 19 (1987) 59.
11. Espinosa, M. Efecto de Diferentes Protocolos para IATF sobre las tasas de preñez aplicados en Ganado lechero. IRAC Cordoba 2010.
12. D. H. Hale, R. B. Symington. Control of sexual activity in ranch cows by intramuscular and intravaginal administration of progestogens. J. Reprod. Fértil. 18 (1969) 193-199.
13. Heba F Salem. Sustained-release progesterone nanosuspension following intramuscular injection in ovariectomized rats. International Journal of Nanomedicine 9 noviembre 2010.
14. P. G. Hignett, H. Boyd, D. F. Wishart. Syncronisation of oestrus in Ayrshire heifers by the use of progestinated intravaginal pessaries. Vet. Rec. 86 (1970) 528-531.
15. Th. Hornykiewytsch. Intra-vaginal application system (INVAS) for controlled drug reléase in animáis. Acta Pharm. Technol. 34 (1988) 68. 145 D. Hiller.
16. Th. Hornykiewytsch. Process for preparing an intravaginal application system. U.S. Pat. No. 5,398,698 (1995).
17. Y. Iwazumi, Y. Fukui, R. B. Vargas, C. Nakano, N. Sato, M. Furudate, K. Ohsaki, S. Matsuzaki. Superovulation using CIDR in Holstein cows. J. Reprod. Dev. 40 (1994) 259-266.
18. D. R. Kerr, M. R. McGowan, C. L. Carroll, F. C. Baldock. Evaluation of three estrus synchronization regimens for use in extensively managed Bos indicus and Bos indicus/taurus heifers in Northern Australia. Theriogenology 36 (1991) 129-141.

19. Lowman, B. G., Scott, N., & Somerville, S. (1976). Condition scoring of cattle. East of Scotland College of Agriculture, Edinburgh. Vol 6 pp. 1-31.
20. S. McDougall, C. R. Burke, K. L. Macmillan, N. B. Williamson. The effect of pretreatment with progesterone on the oestrus response to oestradiol-17b benzoate in the postpartum dairy cow. Proc. NZ Soc. Anim. Prod. 52 (1992) 157-160.
21. W. H. McMillan, K. L. Macmillan. CIDR-B for managed reproduction in beef cows and heifers. Proc. NZ Soc. Anim. Prod. 49 (1989) 85-89.
22. W. H. McMillan, K. L. Macmillan, A. J. Peterson. Is uterine function compromised in heifers synchronised with a long duration progesterone treatment? Proc. Aust. Soc. Reprod. Biol. 25 (1993) 18.
23. K. L. Macmillan, A. M. Day, V. K. Taufa, B. R. Barnes, T. J. Braggins. Plasma progesterone concentration and oestrus or ovulation in heifers treated with CIDR-type B for at least 7 weeks. Proc. Aust. Soc. Reprod. Biol. 19 (1987) 61.
24. K. L. Macmillan, D. R. Barnes, V. K. Taufa, S. N. Duncan. Plasma progesterone concentrations (PPC) in heifers treated with the CIDR type-B. Proc. Asian/Aust. Assoc. Anim. Prod. 4 (1987) 229.
25. K. L. Macmillan, V. K. Taufa. Effects of using bovine CIDR after first insemination on pregnancy rate and subsequent synchrony. Proc. Asian/Aust. Assoc. Anim. Prod. 4 (1987) 224.
26. K. L. Macmillan, V. K. Taufa, A. M. Day. Onset of oestrus and fertility in heifers synchronised with progesterone from a CIDR-Type B for fifteen days. Proc. 1 lth Int. Cong. Anim. Reprod. 4 (1988) 444.
27. K. L. Macmillan, V. K. Taufa, D. R. Barnes, A. M. Day, R. Henry. Detecting estrus in synchronized heifers using tailpaint and an aerosol raddle. Theriogenology 30 (1988) 1099-1114.
28. K. L. Macmillan, S. P. Washburn, H. V. Henderson, S. F. Petch. Effects of varying the progesterone conterní of CIDR intravaginal devices and múltiple CIDR treatments on plasma hormone concentrations and residual hormone conterní. Proc. NZ Soc. Anim. Prod. 50 (1990) 471-472.
29. K. L. Macmillan, V. K. Taufa, A. M. Day, A. J. Peterson. Effects on supplemental progesterone on pregnancy rates in cattle. J. Reprod. Fértil. 43 (1990) 304.
30. K. L. Macmillan, V. K. Taufa, A. M. Day, D. R. Barnes. Some effects of administering progesterone per vaginum during metoestrus on oestrous cycle length in heifers. Proc. Aust. Soc. Reprod. Biol. 21 (1989) 105.36 (1991) 4.
31. K. L. Macmillan, V. K. Taufa, A. M. Day. Combination treatments for synchronising oestrus in dairy heifers. Proc. NZ Soc. Anim. Prod. 53 (1993) 267-270.
32. K. L. Macmillan, V. K. Taufa, A. M. Day, S. McDougall. Some effects of using progesterone and oestradiol benzoate to stimulate oestrus and ovulation in dairy cows with anovulatory anoestrus. Proc. NZ Soc. Anim. Prod. 55 (1995) 239-241.
33. S. R. McPhee, C. J. Hughes, L. D. Staples, M. B. White, A. H. Williams, I. F. Davis, L. P. Cahill. Synchronisation of oestrus in dairy cows using progesterone administered by controlled internal drug reléase (CIDR) devices. Proc. Aust. Soc. Anim. Prod. 16 (1976) 103-106.
34. R. W. Moore, J. F. Smith. Effect of progestogen intravaginal sponges and PMSG on synchronization of oestrus in maiden heifers and on interval from calving to oestrus in beef cows. NZ J. Expt. Agrie. 8 (1980) 199-203.
35. A. J. Peterson, H. C. Henderson. Plasma progesterone concentrations in ovariectomized dairy cows treated with a CIDR-B breeding device. J. Reprod. Fértil. Suppl. 43 (1990) 315.
36. Rathbone, M. Delivering drugs to farmed animals using controlled reléase science and technology. (2012).
37. J. F. Roche, J. P. Crowley, The use of implants containing steroids for growth promotion and control of oestrus in cattle. Anim. Prod. 13 (1971) 385.
38. J. F. Roche, J. P. Crowley. The long-term suppression of heat in cattle with implants of melengestrol acétate. Anim. Prod. 16 (1973) 245-250.
39. J. F. Roche. Effect of short-term progesterone treatment on estrus response and fertility in heifers. J. Reprod. Fértil. 40 (1974) 433-440.
40. J. F. Roche, Synchronisation of oestrus in heifers with implants of progesterone. J. Reprod. Fértil. 41 (1974) 337-344.
41. J. F. Roche. Control of time of ovulation in heifers treated with progesterone and gonadotrophin releasing hormone. J. Reprod. Fértil. 43 (1975) 471-477.
42. J. F. Roche. Retention rate in cows and heifers of intravaginal silastic coils impregnated with progesterone. J. Reprod. Fértil. 46 (1976) 253-255.
43. J. F. Roche. Fertility in cows after treatment with a prostaglandin analogue with or without progesterone. J. Reprod. Fértil. 46 (1976) 341-345.
44. J. F. Roche. Control of oestrus in cattle. World Rev. Anim. Prod. 15 (1979) 49-76.
45. J. F. Roche, J. J. Ireland. Effect of exogenous progesterone on time of occurrence of the LH surge in heifers. J. Anim. Sci. 52 (1981) 580-586.
46. J. D. Savio, W. W. Thatcher, G. R. Morris, K. Entwistle, M. Drost, M. R. Mattiacci. Effects of induction of low plasma progesterone concentrations with a progesterone-releasing intravaginal device on follicular turnover and fertility in cattle. J. Reprod. Fértil. 98 (1993) 77-84.
47. P. F. Scanlon, T. D. Burgess. Subcutaneous and oral applications of progestogens for control of estrus in heifers. Can. J. Anim. Sci. 51 (1971) 540-541.
48. P. F. Scanlon, W. J. Neville, T. G. Burgess, J. W. Macpherson. Synchronisation of oestrus in cattle by intravaginal application of progesterone with oestrogen administration. Can. J. Anim. Sci. 51 (1971) 250-251.
49. P. F. Scanlon, B. Sreenan, I. Gordon. Synchronization of oestrus in heifers by intravaginal application of progesterone. Vet. Rec. 90 (1972) 440^41.
50. H. Shimizu, Y. Toyoda, S. Takeuchi, T. Kawai, S. Adachi. Synchronisation of oestrus and subsequent fertility of beef cattle following the intravaginal administration of gestagen. J. Reprod. Fértil. 13 (1967) 555-558.
51. R. E. Short, R. A. Bellows, J. B. Carr, R. B. Staigmiller, R. D. Randel. Induced or synchronized puberty in heifers. J. Anim. Sci. 43 (1976) 1254-1258.
52. J. Sirois, J. E. Fortune. Lengthening the bovine estrus cycle with low levéis of exogenous progesterone: a model for studying ovarian follicular dominance. Endocrinology 127 (1990) 916-925.
53. J. F. Smith. Synchronisation of oestrus in cattle. NZ J. Agrie. Aug. (1974) 26-30.
54. J. F. Smith, R. J. Fairclough, A. J. Peterson. Plasma levéis of progesterone provera oestradiol-17b and 13, 14 dihydro-15-keto-prostaglandin F in cows treated with Provera-impregnated intravaginal sponges. J. Reprod. Fértil. 55 (1979) 359-364.
55. R. D. Smith, R. J. Pomerantz, W. E. Beale, J. P. McCann, T. E. Pilbeam, W. Hansel. Insemination of Holstein heifers at a preset time after estrus cycle synchronization using progesterone and prostaglandin. J. Anim. Sci. 58 (1984) 792-800.
56. J. Sreenan. Retention of intravaginal sponge-pessaries by cattle. Vet. Rec. 94 (1974) 45-47.
57. L. V. Swanson, B. W. Wickham, K. L. Macmillan. Effect of exogenous progesterone (P4) on follicular waves in dairy beef heifers. J. Dairy Sci. 73 (1990) 177.
58. Valderrama, R. U., & Vélez, E. R. (2014). Uso de dispositivos auriculares de nogestomet en inseminación artificial a tiempo fijo en bovinos doble propósito, con amamantamiento permanente (Using nogestomet ear devices fixed-time insemination artificial in cattle double purpose, permanent nursing c. Revista CES Medicina Veterinaria y Zootecnia, 7(1), 63-71.
59. J. Van Cleeff, K. L. Macmillan, W. W. Thatcher, M. C. Lucy. Estrus synchronization and fertility in heifers with CIDR before and after insemination. J. Anim. Sci. 67 (1989) 383.
60. J. van Cleeff, M. C. Lucy, C. J. Wilcox, W. W. Thatcher. Plasma and milk progesterone and plasma LH in ovariectomized lactating cows treated with new or used controlled internal reléase devices. Anim. Reprod. Sci. 27 (1992) 91-106.
61. S. P. Washburn, H. G. Howard, W. Jochle, K. L. Macmillan. Control of estrus cycles in mature dairy heifers with a progesterone-releasing device. J. Anim. Sci. 67 (1989) 382.
62. R. A. S. Welch. Mating heifers with CIDR. Proc. Ruakura Farmers Conf. 37 (1985) 105-107.
63. J. N. Wiltbank, J. C. Sturges, D. Wideman, D. G. LeFever, L. C. Faulkner. Control of estrus and ovulation using subcutaneous implants and estrogens in beef cattle. J. Anim. Sci. 33 (1971) 600-606.
64. V. W. Winkler, S. Borodkin, S. K. Webel, J. T. Mannebach. In vitro and in vivo considerations of a novel matrix controlled bovine progesterone-releasing intravaginal device. J. Pharm. Sci. 66 (1977) 816-818.
65. D. F. Wishart, B. D. Hoskin. Synchronization of oestrus in heifers using intra-vaginal pessaries impregnated with SC-9880 and PMSG. J. Reprod. Fértil. 17 (1968) 285-289.
66. C. O. Woody, R. A. Pierce, Influence of day of estrus cycle at treatment on response to estrus cycle regulation by norethanrolone implants and estradiol valerate injections, J. Anim. Sci. 39 (1974) 903-906.
67. Z. Z. Xu, L. J. Burton, K. L. Macmillan. Reproductive performance of synchronised lactating dairy cows. Proc. NZ Soc. Anim. Prod. 55 (1995) 242-244.

PATENT REFERENCES

1. CN101152186
2. CN101856361
3. CN103284955
4. MX PA06015172
5. U.S. Pat. No. 7,157,102
6. U.S. Pat. No. 4,599,227
7. WO1991019484
8. WO1999042110
9. WO 2003065924
10. WO2005048930
11. WO2007062483
12. WO2001070200
13. WO 2010085363
14. WO 2011074931
15. WO2012156561
16. WO2013192250
17. US2003/0077297A1
18. US2002/0013304A1
19. YS2014/0271882A1
20. US2013/0108737A1
21. US2009/0220613A1
22. US2003/0180368A1

The invention claimed is:

1. A controlled release injectable formulation, comprising
one or more hormones comprising from about 1 mg/mL to about 250 mg/mL progesterone or an analogue or a salt thereof;
one or more pharmaceutically acceptable organic solvents comprising about 1000 mg/mL or less benzyl alcohol, about 60 mg/mL or less benzyl benzoate, and about 300 mg/mL or less ethanol;
one or more pharmaceutically acceptable fatty acids comprising about 60 mg/mL or less stearic acid;
one or more pharmaceutically acceptable surfactants comprising about 120 mg/mL or less ethoxylated castor oil at 40 moles of ethylene oxide;
one or more pharmaceutically acceptable gel forming agents comprising about 120 mg/mL or less poly(ethylene glycol)-block-poly(propylene glycol)-block-poly (ethylene glycol); and
about 1000 mg/mL or less water;
wherein a portion of said one or more hormones is dissolved in a mixture comprising said one or more pharmaceutically acceptable organic solvents to form a free portion, and a portion of said one or more hormones is enclosed by said one or more pharmaceutically acceptable fatty acids to form an enclosed portion,
wherein said free and enclosed portions are included in a matrix, said matrix comprising said one or more pharmaceutically acceptable gel forming agents and said one or more pharmaceutically acceptable surfactants, and
wherein the formulation is suitable for administration by an injection method selected from the group consisting of a subcutaneous, intravenous, intraparenteral, intramuscular and intradermal injection.

2. The controlled release injectable formulation of claim 1, further comprising a pharmaceutically acceptable oily carrier other than the said one or more pharmaceutically acceptable fatty acids, wherein the portion of said one or more hormones is dissolved in a mixture comprising said one or more pharmaceutically acceptable organic solvents and said pharmaceutically acceptable oily carrier.

3. The controlled release injectable formulation of claim 1, wherein the matrix further comprises one or more pharmaceutically acceptable structure forming agents.

4. The controlled release injectable formulation of claim 2, wherein the matrix further comprises one or more pharmaceutically acceptable structure forming agents.

5. The controlled release injectable formulation of claim 1, wherein the formulation is configured to increase the likelihood that a female mammal becomes pregnant, to synchronize the ovulation of a group of female mammals, to reduce the anestrous period in a female mammal, or combinations thereof.

6. The formulation of claim 2, wherein said pharmaceutically acceptable oily carrier is selected from the group consisting of flax oil, sesame oil, refined sesame oil, castor oil, palmitic acid, soybean oil, ethoxylated soybean oil, sunflower oil, corn oil, coconut oil, olive oil, almond oil, cotton oil, and combinations thereof.

7. The formulation of claim 6, wherein that said pharmaceutically acceptable oily carrier comprises refined sesame oil.

8. The formulation of claim 4, wherein said one or more pharmaceutically acceptable structure forming agents are selected from the group consisting of cellulose, a cellulose derivative, microcrystalline cellulose, ethylcellulose, hydroxyethylcellulose, hydroxyethylmethylcellulose, hydroxyethylpropylcellulose, carboxymethylcellulose, guar gum, gum arabic, xanthan gum, chitosan, alginate, gelatin, carbomer homopolymer or poly(acrylic acid) or 2-propenoic acid homopolymer, sodium starch glycolate, sodium corscarmelosa, alginic acid, pectin, and combinations thereof.

9. The formulation of claim 8, wherein said one or more pharmaceutically acceptable structure forming agents are selected from the group consisting of hydroxyethyl cellulose, gum arabic, xanthan gum and combinations thereof.

10. The formulation of claim 8, wherein said one or more pharmaceutically acceptable structure forming agents comprise hydroxyethyl cellulose.

11. The formulation of claim 1, further comprising about 50 mg/mL or less hydroxyethyl cellulose.

12. The formulation of claim 1, further comprising about 100 mg/mL or less refined sesame oil.

13. The formulation of claim 1, wherein the formulation has a pH from about 4.0 to about 8.0.

14. The formulation of claim 1, further comprising a pharmaceutically acceptable antioxidant agent selected from the group consisting of Vitamin E, d-a-tocopherol propylene glycol 1000 succinate, Butylhydroxytoluene (BHT), Butylhydroxyanisol (BHA), sodium bisulfite, ascorbic acid, ascorbyl palmitate, Vitamin A, propyl gallate, monothioglycerol, sodium sulfoxylate formal, and combinations thereof.

15. The formulation of claim 1, wherein the formulation is suitable for administration by intramuscular injection.

16. The formulation of claim 1, wherein upon administration to a female mammal there is a sustained blood concentration of said one or more hormones followed by a decrease in blood hormone concentration.

17. The formulation of claim 16, wherein the decrease in blood concentration of the hormone takes place from about 5 to about 10 days after administration of the formulation.

18. The formulation of claim 17, wherein the decrease in blood concentration of the hormone takes place from about 6 to about 8 days after administration of the formulation.

19. The formulation of claim 1, wherein from 1 to 20 mL of said formulation forms a dosage unit.

20. A prefilled syringe comprising a dosage unit according to claim 19.

21. A kit comprising a dosage unit according to claim 19, together with instructions for use.

22. A process for preparing the formulation according to claim 1, comprising:
i) preparing a first solution comprising said one or more pharmaceutically acceptable surfactants and water;
ii) preparing a second solution comprising said one or more hormones, said pharmaceutically acceptable fatty acid, said one or more pharmaceutically acceptable organic solvents, said one or more pharmaceutically acceptable gel forming agents and said water, wherein said second solution is prepared by combining mixtures I and II, wherein
a) mixture I comprises said one or more hormones, said one or more pharmaceutically acceptable fatty acids and said one or more pharmaceutically acceptable organic solvents; and
b) mixture II comprises said one or more pharmaceutically acceptable gel forming agents and water;
iii) preparing a third solution comprising said one or more hormones and said one or more pharmaceutically acceptable organic solvents;
iv) combining said first solution with said second solution; and
v) incorporating into the mixture obtained in step iv) said third solution.

23. The process of claim 22, wherein the third solution further comprises a pharmaceutically acceptable oily carrier.

24. The process of claim 22, further comprising preparing a fourth solution including one or more pharmaceutically acceptable structure forming agents and water.

25. The process of claim 24, comprising adding to the mixture obtained in step v) said fourth solution.

26. A method for controlling the reproductive cycle and ovulation of a female mammal, increasing the likelihood that a female mammal becomes pregnant, synchronizing the ovulation of a group of female mammals, and/or reducing the anestrous period in a female mammal comprising administering the formulation according to claim 1 to said female mammal.

27. The method of claim 26, wherein said female mammal is selected from cattle, pigs, goats, sheep, horses or camels.

28. The method of claim 26, wherein said female mammal is a reproductively mature bovine animal.

29. The method of claim 26, wherein said formulation is administered to said female animal before insemination.

30. The method of claim 29, wherein the insemination is carried out from about 9 to about 11 days after the administration of said formulation.

31. The method of claim 26, further comprising administration of estradiol benzoate, wherein the administration of estradiol benzoate is performed the same day as the administration of said formulation.

32. The method of claim 26, further comprising administration of prostaglandin, an analogue or a salt thereof, wherein the administration of prostaglandin, an analog or a salt thereof is carried out from about 7 to about 8 days after administering said formulation, two days before administering said formulation, or both two days before administering said formulation and about 7 to about 8 days after administering said formulation.

33. The method of claim 29, further comprising administering the gonadotropin releasing hormone (GnRH), an analogue or a salt thereof, wherein the administration of the gonadotropin releasing hormone (GnRH), an analogue or a salt thereof is carried out on the same day as the insemination or a day before the insemination.

34. The method of claim 26, further comprising administering estradiol cypionate, wherein the administration of estradiol cypionate is carried out from about 7 to about 8 days after the administration of said formulation.

35. The formulation of claim 2, further comprising a pharmaceutically acceptable antioxidant agent selected from the group consisting of Vitamin E, d-a-tocopherol propylene glycol 1000 succinate, Butylhydroxytoluene (BHT), Butylhydroxyanisol (BHA), sodium bisulfite, ascorbic acid, ascorbyl palmitate, Vitamin A, propyl gallate, monothioglycerol, sodium sulfoxylate formal, and combinations thereof.

* * * * *